(12) United States Patent
Gross et al.

(10) Patent No.: US 7,799,096 B2
(45) Date of Patent: Sep. 21, 2010

(54) AGENT FOR DYEING KERATIN-CONTAINING FIBERS

(75) Inventors: Wibke Gross, Hückelhoven (DE); Doris Oberkobusch, Düsseldorf (DE); Ralph Nemitz, Jünchen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 12/514,423

(22) PCT Filed: Nov. 20, 2007

(86) PCT No.: PCT/EP2007/062528

§ 371 (c)(1), (2), (4) Date: May 11, 2009

(87) PCT Pub. No.: WO2008/074578

PCT Pub. Date: Jun. 26, 2008

(65) Prior Publication Data

US 2010/0064450 A1    Mar. 18, 2010

(30) Foreign Application Priority Data

Dec. 18, 2006  (DE) .................. 10 2006 060 150

(51) Int. Cl.
A61Q 5/10     (2006.01)
C07D 239/00   (2006.01)
C07C 47/00    (2006.01)

(52) U.S. Cl. ............. 8/405; 8/406; 8/407; 8/435; 8/565; 8/567; 8/673; 8/608; 8/613; 544/245; 568/420

(58) Field of Classification Search ......... 8/405, 8/406, 435, 565, 567, 673, 608, 613; 544/245; 568/420

See application file for complete search history.

(56) References Cited

U.S. PATENT DOCUMENTS 5,464,856 A    11/1995   Cetenko et al.

FOREIGN PATENT DOCUMENTS

| DE | 3723354 A1 | 1/1989 |
|---|---|---|
| DE | 3725030 A1 | 2/1989 |
| DE | 3926344 A1 | 2/1991 |
| DE | 102005022790 A1 | 11/2006 |
| EP | 0998908 A2 | 5/2000 |
| WO | 2004022016 A1 | 3/2004 |
| WO | WO 2006119819 A1 * | 11/2006 |

OTHER PUBLICATIONS

STIC Search Report dated May 3, 2010.*
Baumann, H., et al. "Reaktionen der Methylenbasen von oxazolidinonen und Pryimidonen," Liebigs Ann. Chem., Bd. 717, 1968, pp. 124-136; and English abstract "Reactions of Methylene Bases of Oxazolidinones and Pyrimidinones."
Gadalla, K.Z., et al "A Facile Synthesis of Substituted Benzimidazoles of Anticipated Biological Activity," Bulletin of the National Research Centre, Egypt, vol. 18, No. 3, 1993, pp. 151-162.
International Search Report for PCT/EP2007/062528 mailed Feb. 17, 2009.

* cited by examiner

Primary Examiner—Eisa B Elhilo
(74) Attorney, Agent, or Firm—David P. LeCroy

(57) ABSTRACT

The invention relates to an agent for dying fibers comprising keratin, particularly human hair, the agent comprising at least one compound of the formula:

$$\text{(I)}$$

[Structure: benzene ring with CHO, OH, $R^3$, $R^4$ substituents and $-CH_2-N(R^1)(R^2)$ group]

together with at least one CH-acidic compound. The invention also relates to methods for shading oxidation dyed fibers, methods for freshening up fibers, methods for making an agent for dyeing fibers and to various compositions.

22 Claims, No Drawings

AGENT FOR DYEING KERATIN-CONTAINING FIBERS

CROSS-REFERENCE TO RELATED APPLICATIONS

This application is a U.S. National Stage entry under 35 U.S.C. §371 based on International Application No. PCT/EP2007/062528, filed 20 Nov. 2007, which was published under PCT Article 21(2) and claims the benefit of the filing date of German Patent Application No 102006060150.5 filed 18 Dec. 2006, the disclosures of which applications are hereby incorporated herein by reference.

TECHNICAL FIELD

The invention relates generally to cosmetic compositions and methods for using such compositions. More particularly, the invention relates to an agent for dyeing keratin-containing fibers, in particular human hair, which contains selected 3-aminomethyl-4-hydroxybenzaldehyde derivatives in combination with CH-acidic compounds, to the use of this combination in agents for dyeing keratin-containing fibers, for freshening up hair color or shading of already dyed keratin-containing fibers and to a method of dyeing keratin-containing fibers, in particular human hair.

BACKGROUND

To dye keratin-containing fibers, use is generally made of either direct dyes or oxidation dyes, which arise through oxidative coupling of one or more developer components with one another or with one or more coupler components. The coupler and developer components are also known as oxidation dye precursors.

The developer components used are conventionally primary aromatic amines with a further free or substituted hydroxyl or amino group located in para or ortho position, diaminopyridine derivatives, heterocyclic hydrazones, 4-aminopyrazolone derivatives and 2,4,5,6-tetraminopyrimidine and the derivatives thereof.

Particular representatives are for example p-phenylenediamine, p-tolylenediamine, 2,4,5,6-tetraminopyrimidine, p-aminophenol, N,N-bis-(2'-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine, 2,5,6-triamino-4-hydroxypyrimidine and 4,5-diamino-1-(2-hydroxyethyl)pyrazole.

The coupler components used are generally m-phenylenediamine derivatives, naphthols, resorcinol and resorcinol derivatives, pyrazolones, m-aminophenols and substituted pyridine derivatives. Particularly suitable coupler substances are α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)-anisole (Lehmann blue), 1-phenyl-3-methylpyrazol-5-one, 2,4-dichloro-3-aminophenol, 1,3-bis-(2,4-diaminophenoxy) propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine.

Although intense dyeing results with good fastness properties may be achieved with oxidation dyes, the color generally develops under the influence of oxidizing agents such as for example $H_2O_2$, which may in some cases result in damage to the fiber. Moreover, some oxidation dye precursors or certain mixtures of oxidation dye precursors occasionally have a sensitizing effect in people with sensitive skin. Direct dyes are applied under gentler conditions, but their disadvantage is that the fastness properties of the dyeing results are often only inadequate.

Accordingly, it is desirable to provide dyeing agents for keratin-containing fibers, in particular human hair, which are at least equal in quality to conventional oxidation dyeing agents with regard to color depth and fastness properties, such as for example light, rubbing and washing fastness and perspiration and cold wave fastness, but without its being essential to use oxidizing agents such as for example $H_2O_2$. In addition, it is desirable to provide dyeing agents that do not have any or have only very slight sensitization potential and have no mutagenic effect.

BRIEF SUMMARY

Agents for dyeing keratin-containing fibers, methods for dyeing keratin-containing fibers, methods for shading oxidation dyed keratin-containing fibers, methods for freshening up keratin-containing fibers dyed with oxidative dyeing agents, methods for making an agent for dyeing keratin-containing fibers, and compounds are provided herein. In accordance with an exemplary embodiment, an agent for dyeing keratin-containing fibers is provided. The agent comprises, in a cosmetic carrier:

as component A at least one compound according to formula I,

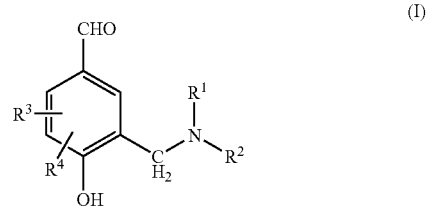

(I)

in which
R$^1$ and R$^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and R$^3$ and R$^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n$NR$^5$R$^6$ group, in which R$^5$ and R$^6$ mutually independently denote a ($C_1$ to $C_6$) alkyl group or a ($C_2$ to $C_6$) monohydroxyalkyl group and n denotes an integer from 0 to 6;

or R$^3$ and R$^4$ may form a five-membered or six-membered aromatic or heteroaromatic ring; and at least one CH-acidic compound as component B.

In accordance with another exemplary embodiment, a method of dyeing keratin-containing fibers is provided. The method comprises the steps of:

applying to the kaeratin-containing fibers an agent comprising, in a cosmetic carrier, a compound according to formula (I)

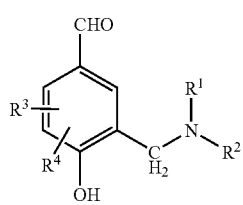

in which

R$^1$ and R$^2$ mutually independently denote a (C$_1$ to C$_6$) alkyl group, a (C$_2$ to C$_6$) alkenyl group, a (C$_1$ to C$_6$) monohydroxyalkyl group, a (C$_2$ to C$_6$) polyhydroxyalkyl group, a (C$_1$ to C$_6$)-alkoxy-(C$_2$ to C$_6$)-alkyl group, an aryl-(C$_1$ to C$_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and R$^3$ and R$^4$ mutually independently denote a hydrogen atom, a halogen atom, a (C$_1$ to C$_6$) alkyl group, a (C$_2$ to C$_6$) alkenyl group, a hydroxy group, a (C$_1$ to C$_6$) alkoxy group, a (C$_1$ to C$_6$) monohydroxyalkyl group, a (C$_2$ to C$_6$) polyhydroxyalkyl group, a hydroxy-(C$_1$ to C$_6$)-alkyloxy group, a piperidin-1-ylmethyl group, a pyrrolidin-1-ylmethyl group, a morpholin-4-ylmethyl group or a —(CH$_2$)$_n$NR$^5$R$^6$ group, in which R$^5$ and R$^6$ mutually independently denote a (C$_1$ to C$_6$) alkyl group or a (C$_2$ to C$_6$) monohydroxyalkyl group and n denotes an integer from 0 to 6; or R$^3$ and R$^4$ may form a five-membered or six-membered aromatic or heteroaromatic ring;

leaving the agent on the keratin-containing fibers for a period of time; and rinsing the agent out of the keratin-containing fibers or washing the agent out of the keratin-containing fibers with a shampoo.

In accordance with a further exemplary embodiment, a method for shading oxidation dyed keratin-containing fibers is provided. The method comprises the steps of:

applying to the keratin-containing fibers an agent comprising, as component A at least one compound according to formula I,

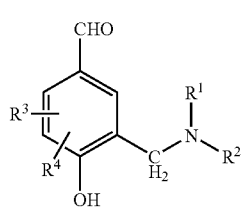

in which

R$^1$ and R$^2$ mutually independently denote a (C$_1$ to C$_6$) alkyl group, a (C$_2$ to C$_6$) alkenyl group, a (C$_1$ to C$_6$) monohydroxyalkyl group, a (C$_2$ to C$_6$) polyhydroxyalkyl group, a (C$_1$ to C$_6$)-alkoxy-(C$_2$ to C$_6$)-alkyl group, an aryl-(C$_1$ to C$_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and R$^3$ and R$^4$ mutually independently denote a hydrogen atom, a halogen atom, a (C$_1$ to C$_6$) alkyl group, a (C$_2$ to C$_6$) alkenyl group, a hydroxy group, a (C$_1$ to C$_6$) alkoxy group, a (C$_1$ to C$_6$) monohydroxyalkyl group, a (C$_2$ to C$_6$) polyhydroxyalkyl group, a hydroxy-(C$_1$ to C$_6$)-alkyloxy group, a piperidin-1-ylmethyl group, a pyrrolidin-1-ylmethyl group, a morpholin-4-ylmethyl group or a —(CH$_2$)$_n$NR$^5$R$^6$ group, in which R$^5$ and R$^6$ mutually independently denote a (C$_1$ to C$_6$) alkyl group or a (C$_2$ to C$_6$) monohydroxyalkyl group and n denotes an integer from 0 to 6; or R$^3$ and R$^4$ may form a five-membered or six-membered aromatic or heteroaromatic ring; and at least one CH-acidic compound as component B.

In accordance with another exemplary embodiment, a method for freshening up keratin-containing fibers dyed with oxidative dyeing agents is provided. The method comprises the steps of:

applying to the keratin-containing fibers an agent comprising:

as component A at least one compound according to formula I,

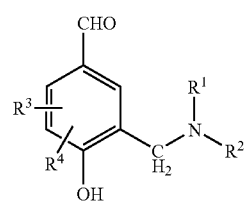

in which

R$^1$ and R$^2$ mutually independently denote a (C$_1$ to C$_6$) alkyl group, a (C$_2$ to C$_6$) alkenyl group, a (C$_1$ to C$_6$) monohydroxyalkyl group, a (C$_2$ to C$_6$) polyhydroxyalkyl group, a (C$_1$ to C$_6$)-alkoxy-(C$_2$ to C$_6$)-alkyl group, an aryl-(C$_1$ to C$_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and R$^3$ and R$^4$ mutually independently denote a hydrogen atom, a halogen atom, a (C$_1$ to C$_6$) alkyl group, a (C$_2$ to C$_6$) alkenyl group, a hydroxy group, a (C$_1$ to C$_6$) alkoxy group, a (C$_1$ to C$_6$) monohydroxyalkyl group, a (C$_2$ to C$_6$) polyhydroxyalkyl group, a hydroxy-(C$_1$ to C$_6$)-alkyloxy group, a piperidin-1-ylmethyl group, a pyrrolidin-1-ylmethyl group, a morpholin-4-ylmethyl group or a —(CH$_2$)$_n$NR$^5$R$^6$ group, in which R$^5$ and R$^6$ mutually independently denote a (C$_1$ to C$_6$) alkyl group or a (C$_2$ to C$_6$) monohydroxyalkyl group and n denotes an integer from 0 to 6; or R$^3$ and $R^4$ may form a five-membered or six-membered aromatic or heteroaromatic ring; and at least one CH-acidic compound as component B.

In accordance with yet another exemplary embodiment, a compound is provided of the formula (V)

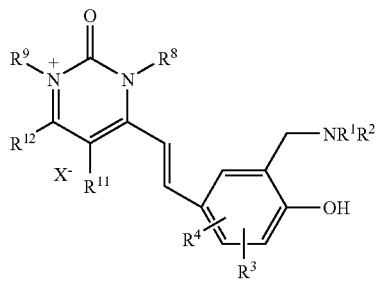

(V)

in which:
- $R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and may optionally contains at least one additional heteroatom selected from nitrogen, oxygen or sulfur;
- $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a $-(CH_2)_nNR^5R^6$ group,
  - in which $R^5$ and $R^6$ mutually independently denote a ($C_1$ to $C_6$) alkyl group or a ($C_2$ to $C_6$) monohydroxyalkyl group and n denotes an integer from 0 to 6,
  - or $R^3$ and $R^4$ form a five-membered or six-membered aromatic or heteroaromatic ring;
- $R^8$ and $R^9$ mutually independently denote a linear or cyclic $C_1$-$C_6$ alkyl group, a $C_2$-$C_6$ alkenyl group, an optionally substituted aryl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$-alkoxy-$C_1$-$C_6$-alkyl group, an $R^{IV}R^VN-(CH_2)_p-$ group, in which $R^{IV}$ and $R^V$ mutually independently denote a hydrogen atom, a $C_1$-$C_4$ alkyl group, a $C_1$-$C_4$ hydroxyalkyl group or an aryl-$C_1$-$C_6$-alkyl group, wherein $R^{IV}$ and $R^V$, together with the nitrogen atom, optionally form a 5-, 6- or 7-membered ring and p denotes a number 2, 3, 4, 5 or 6;
- $R^{11}$ denotes a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, an $R^{VI}R^{VII}N-(CH_2)_q-$ group, in which $R^{VI}$ and $R^{VII}$ mutually independently denote a hydrogen atom, a $C_1$-$C_6$ alkyl group, a $C_1$-$C_6$ hydroxyalkyl group or an aryl-$C_1$-$C_6$-alkyl group, and q denotes a number 1, 2, 3, 4, 5 or 6, wherein the residue $R^{11}$, together with one of the residues $R^{12}$, optionally forms a 5- or 6-membered aromatic ring, which may optionally be substituted with a halogen atom, a ($C_1$-$C_6$) alkyl group, a $C_1$-$C_6$ hydroxyalkyl group, a $C_2$-$C_6$ polyhydroxyalkyl group, a ($C_1$-$C_6$) alkoxy group, a $C_1$-$C_6$ hydroxyalkoxy group, a nitro group, a hydroxy group, an $R^{VIII}R^{IX}N-(CH_2)_s-$ group, in which $R^{VIII}$ and $R^{IX}$ mutually independently denote a hydrogen atom, a $C_1$-$C_6$ alkyl group, a $C_1$-$C_6$ hydroxyalkyl group or an aryl-$C_1$-$C_6$-alkyl group, and s denotes a number 0, 1, 2, 3, 4, 5 or 6;
- $R^{12}$ denotes a hydrogen atom or a $C_1$-$C_6$ alkyl group; and
- $X^-$ denotes a physiologically acceptable anion.

In accordance with a further exemplary embodiment, a compound is provided of the formula (VI)

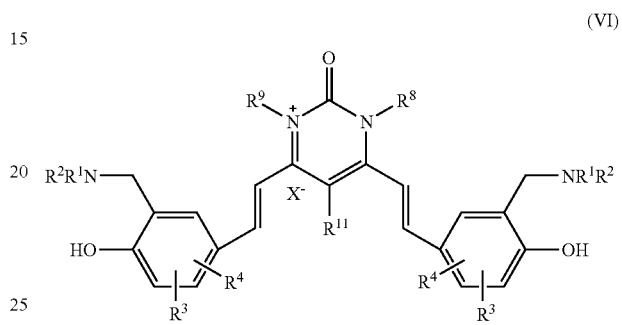

(VI)

in which:
- $R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur;
- $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a $-(CH_2)_nNR^5R^6$ group,
  - in which $R^5$ and $R^6$ mutually independently denote a ($C_1$ to $C_6$) alkyl group or a ($C_2$ to $C_6$) monohydroxyalkyl group and n denotes an integer from 0 to 6,
  - or $R^3$ and $R^4$ form a five-membered or six-membered aromatic or heteroaromatic ring;
- $R^8$ and $R^9$ mutually independently denote a linear or cyclic $C_1$-$C_6$ alkyl group, a $C_2$-$C_6$ alkenyl group, an optionally substituted aryl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$-alkoxy-$C_1$-$C_6$-alkyl group, an $R^{IV}R^VN-(CH_2)_p-$ group, in which $R^{IV}$ and $R^V$ mutually independently denote a hydrogen atom, a $C_1$-$C_4$ alkyl group, a $C_1$-$C_4$ hydroxyalkyl group or an aryl-$C_1$-$C_6$-alkyl group, wherein $R^{IV}$ and $R^V$, together with the nitrogen atom, optionally form a 5-, 6- or 7-membered ring and p denotes a number 2, 3, 4, 5 or 6;
- $R^{11}$ denotes a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, an $R^{VI}R^{VII}N-(CH_2)_q-$ group, in which $R^{VI}$ and $R^{VII}$ mutually independently denote a hydrogen atom, a $C_1$-$C_6$ alkyl group, a $C_1$-$C_6$ hydroxyalkyl group or an aryl-$C_1$-$C_6$-alkyl group, and q denotes a number 1, 2, 3, 4, 5 or 6, wherein the residue $R^{11}$, together with one of the residues $R^{12}$, optionally forms a 5- or 6-membered aromatic ring, which may optionally be substituted with a halogen atom, a ($C_1$-$C_6$) alkyl group, a $C_1$-$C_6$ hydroxyalkyl group, a $C_2$-$C_6$ polyhydroxyalkyl group, a ($C_1$-$C_6$) alkoxy group, a $C_1$-$C_6$ hydroxyalkoxy group, a nitro group, a hydroxy group, an $R^{VIII}R^{IX}N$—$(CH_2)_s$— group, in which $R^{VIII}$ and $R^{IX}$ mutually independently denote a hydrogen atom, a $C_1$-$C_6$ alkyl group, a $C_1$-$C_6$ hydroxyalkyl group or an aryl-$C_1$-$C_6$-alkyl group, and s denotes a number 0, 1, 2, 3, 4, 5 or 6; and $X^-$ denotes a physiologically acceptable anion.

In accordance with another exemplary embodiment, a compound is provided of the formula (VII)

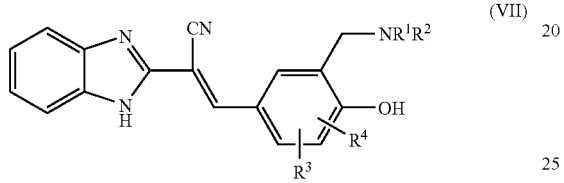

(VII)

in which:
$R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5 R^6$ group, and in which $R^5$ and $R^6$ mutually independently denote a ($C_1$ to $C_6$) alkyl group or a ($C_2$ to $C_6$) monohydroxyalkyl group and n denotes an integer from 0 to 6, or $R^3$ and $R^4$ form a five-membered or six-membered aromatic or heteroaromatic ring.

In accordance with another exemplary embodiment, s method for making an agent for dyeing keratin-containing fibers is provided. The method comprises the steps of:

providing a compound according to formula (I)

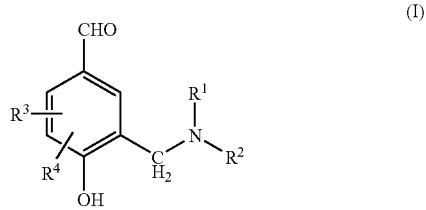

(I)

in which
$R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5 R^6$ group, in which $R^5$ and $R^6$ mutually independently denote a ($C_1$ to $C_6$) alkyl group or a ($C_2$ to $C_6$) monohydroxyalkyl group and n denotes an integer from 0 to 6, or $R^3$ and $R^4$ may form a five-membered or six-membered aromatic or heteroaromatic ring; and combining the compound according to formula (I) with at least one CH-acidic compound.

DETAILED DESCRIPTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Dyeing agents containing compounds according to the formula I below in combination with CH-acidic compounds, and the use of this combination for dyeing keratin-containing fibers or for freshening up color or shading of already dyed keratin-containing fibers are hitherto unknown.

Patent application WO-A1-2004/022016 discloses CH-acidic 1,2-dihydropyrimidinium derivatives, which are suitable, in combination with reactive carbonyl compounds, in particular benzaldehyde derivatives, for dyeing keratin-containing fibers. Benzaldehydes with the substitution pattern of the compounds as per the formula I below are not mentioned therein, however.

It has surprisingly now been found that the compounds represented in formula I are very highly suitable in combination with CH-acidic compounds for dyeing keratin-containing fibers even in the absence of oxidizing agents. They produce coloration with excellent brightness and color depth and result in a multiplicity of color shades. The coloration obtained in particular also has improved fastness properties over a shade range covering red, reddish purple, purple or blue. However, the use of oxidizing agents should not be ruled out in principle. In addition, the benzaldehyde derivatives contemplated herein distinguished by increased physiological compatibility.

In an exemplary embodiment of the present invention, an agent for dyeing keratin-containing fibers, in particular human hair, contains in a cosmetic carrier:

as component A at least one compound according to the formula I,

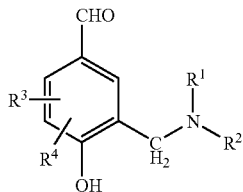

in which:
R$^1$ and R$^2$ mutually independently denote a (C$_1$ to C$_6$) alkyl group, a (C$_2$ to C$_6$) alkenyl group, a (C$_1$ to C$_6$) monohydroxyalkyl group, a (C$_2$ to C$_6$) polyhydroxyalkyl group, a (C$_1$ to C$_6$)-alkoxy-(C$_2$ to C$_6$)-alkyl group, an aryl-(C$_1$ to C$_6$)-alkyl group or the two residues form together with the nitrogen atom a five-membered, six-membered, seven-membered or eight-membered heterocyclic ring, which is saturated or unsaturated, is optionally substituted and may optionally contain at least one additional heteroatom selected from nitrogen, oxygen or sulfur;

R$^3$ and R$^4$ mutually independently denote a hydrogen atom, a halogen atom, a (C$_1$ to C$_6$) alkyl group, a (C$_2$ to C$_6$) alkenyl group, a hydroxy group, a (C$_1$ to C$_6$) alkoxy group, a (C$_1$ to C$_6$) monohydroxyalkyl group, a (C$_2$ to C$_6$) polyhydroxyalkyl group, a hydroxy-(C$_1$ to C$_6$)-alkyloxy group, a piperidin-1-ylmethyl group, a pyrrolidin-1-ylmethyl group, a morpholin-4-ylmethyl group or a —(CH$_2$)$_n$NR$^5$R$^6$ group, in which R$^5$ and R$^6$ mutually independently denote a (C$_1$ to C$_6$) alkyl group or a (C$_2$ to C$_6$) monohydroxyalkyl group and n denotes an integer from 0 to 6, or R$^3$ and R$^4$ may form a five-membered or six-membered aromatic or heteroaromatic ring, together with.

at least one CH-acidic compound as component B.

Keratin-containing fibers should here be taken to mean wool, furs, feathers and in particular human hair. The dyeing agents contemplated herein may however in principle also be used to dye other natural fibers, such as for example cotton, jute, sisal, linen or silk, modified natural fibers, such as for example regenerated cellulose, nitro-, alkyl- or hydroxyalkylcellulose or cellulose acetate.

Examples of C$_1$-C$_6$ alkyl residues are the groups methyl, ethyl, propyl, isopropyl, n-butyl, sec-butyl and tert.-butyl, n-pentyl and n-hexyl. Propyl, ethyl and methyl are preferred alkyl residues. Examples of corresponding cyclic alkyl groups are cyclopentyl and cyclohexyl. Examples of preferred (C$_2$ to C$_6$) alkenyl residues are vinyl and allyl.

A hydroxymethyl, 2-hydroxyethyl, 2-hydroxypropyl, 3-hydroxypropyl, 4-hydroxybutyl, 5-hydroxypentyl and a 6-hydroxyethyl group may furthermore be mentioned as preferred examples of a C$_1$ to C$_6$ monohydroxyalkyl group. A 2-hydroxyethyl group is particularly preferred.

Examples of a (C$_2$ to C$_6$) polyhydroxyalkyl group are the 2,3-dihydroxypropyl group, the 3,4-dihydroxybutyl group and the 2,4-dihydroxybutyl group.

In a preferred embodiment, C$_1$ to C$_6$ alkoxy groups are for example a methoxy or an ethoxy group.

The methoxyethyl, ethoxyethyl, methoxypropyl, methoxybutyl, ethoxybutyl and methoxyhexyl groups are examples of (C$_1$ to C$_6$)-alkoxy-(C$_2$ to C$_6$)-alkyl groups.

A preferred hydroxy-(C$_1$-C$_6$)-alkoxy group is the 2-hydroxyethoxy group.

Examples of halogen atoms are F, Cl, Br or I atoms, Br and Cl atoms being very particularly preferred.

The aminomethyl, 2-aminoethyl, 3-aminopropyl, 2-dimethylaminoethyl, diethylaminomethyl, dimethylaminomethyl, 2-methylaminoethyl, dimethylamino, 1-piperidinomethyl, 1-pyrrolidinomethyl, 4-morpholinomethyl, bis(2-hydroxyethyl)amino and the amino group are examples of an R$^5$R$^6$N—(CH$_2$)$_n$— group, the diethylaminomethyl, 1-piperidinomethyl, 2-dimethylaminoethyl, dimethylamino and the amino group being preferred. Preferred aryl-(C$_1$ to C$_6$)-alkyl groups are benzyl and 2-phenylethyl.

In a preferred embodiment, in compounds according to the formula (I), the residues R$^1$ and R$^2$ mutually independently denote a (C$_1$ to C$_6$) alkyl group, a (C$_1$ to C$_6$) monohydroxyalkyl group or an aryl-(C$_1$ to C$_6$)-alkyl group or the two residues form together with the nitrogen atom a five-membered, six-membered, seven-membered or eight-membered heterocyclic ring, which is saturated or unsaturated, is optionally substituted, and may optionally contain at least one additional heteroatom selected from nitrogen, oxygen or sulfur.

In a more preferred embodiment, according to the formula (I) the residues R$^1$ and R$^2$ mutually independently denote a (C$_1$ to C$_6$) alkyl group or R$^1$ and R$^2$ form together with the nitrogen atom a group of the formulae (I-1), (I-2) or (I-3)

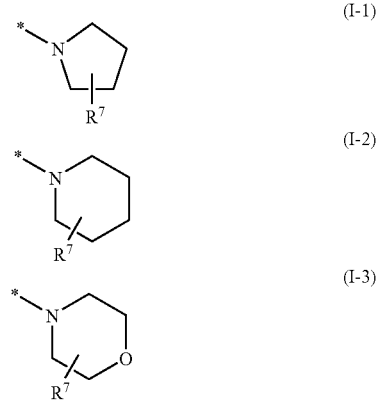

in which R$^7$ means a hydrogen atom, a halogen atom, a hydroxy group, a (C$_1$ to C$_6$) alkyl group, a (C$_1$ to C$_6$) monohydroxyalkyl group, a (C$_2$ to C$_6$) polyhydroxyalkyl group, a (C$_1$ to C$_6$) alkoxy group or an amino group, preferably a hydrogen atom or a hydroxy group. The valence indicated * in the formulae (I-1) to (I-3) denotes the link of the heterocyclic ring via the nitrogen atom to the CH$_2$ fragment of the —CH$_2$—NR$^1$R$^2$ residue according to the formula (I).

According to the formula (I), R$^1$ and R$^2$ very particularly preferably form together with the nitrogen atom a pyrrolidin-1-yl group, a 3-hydroxypyrrolidin-1-yl group, a 4-hydroxypiperidin-1-yl group, a 3-hydroxypiperidin-1-yl group, a piperidin-1-yl group, a morpholin-4-yl group or a (dimethylamino)methyl group.

In all the above-stated embodiments of the formula (I), R$^4$ in turn preferably means a hydrogen atom or a hydroxy group and R$^3$ denotes a fluorine atom, a chlorine atom, a bromine atom, an iodine atom, a hydroxy group or a (C$_1$ to C$_6$) alkoxy group (in particular a chlorine atom, a bromine atom, a hydroxy group or a methoxy group) or R$^3$ and R$^4$ together with the remainder of the molecule form a five-membered or six-membered aromatic or heteroaromatic ring. If the residues R$^3$ and R$^4$ of the formula (I) form, together with the remainder of the molecule, an aromatic or heteroaromatic ring, a six-membered ring is preferred, which in turn is preferably an aromatic, carbocyclic ring.

According to all the above-stated embodiments of the formula (I), it is likewise preferable according to the invention for the substituents $R^3$ and $R^4$ to be linked to the benzene ring, as depicted in formulae (Ia) or (Ib)

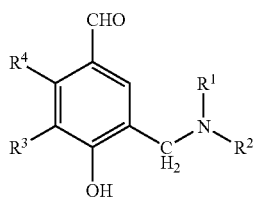
(Ia)

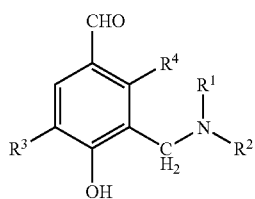
(Ib)

the residues $R^1$, $R^2$, $R^3$ and $R^4$ being defined according to the formula (I) with the proviso that $R^3$ and $R^4$ may form a five-membered or six-membered aromatic or heteroaromatic ring only according to the formula (Ia).

It is particularly preferable for at least one of the following compounds of the formula (I) to be contained in the agent:

| | |
|---|---|
| 3-[(dimethylamino)methyl]-4-hydroxy-5-methoxybenzaldehyde | 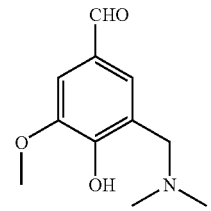 |
| 4-hydroxy-3-methoxy-5-(pyrrolidin-1-ylmethyl)benzaldehyde | 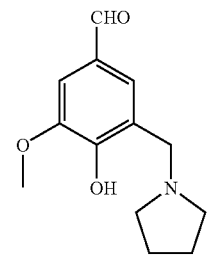 |
| 4-hydroxy-3-methoxy-5-(piperidin-1-ylmethyl)benzaldehyde | 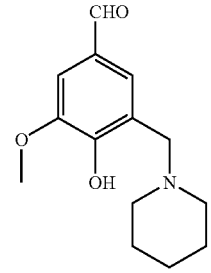 |
| 4-hydroxy-3-[(3-hydroxypyrrolidin-1-yl)methyl]-5-methoxybenzaldehyde | 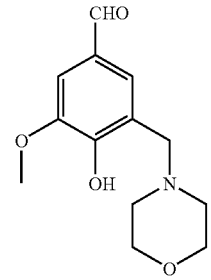 |

-continued
| | |
|---|---|
| 4-hydroxy-3-[(3-hydroxypyrrolidin-1-yl)methyl]-5-methoxybenzaldehyde | 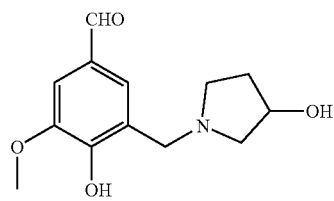 |
| 4-hydroxy-3-[(4-hydroxypiperidin-1-yl)methyl]-5-methoxybenzaldehyde | 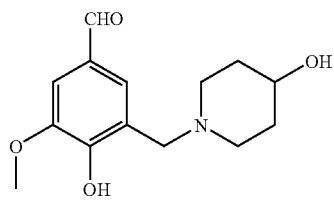 |
| 4-hydroxy-3-[(3-hydroxypiperidin-1-yl)methyl]-5-methoxybenzaldehyde | 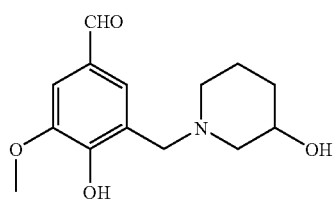 |
| 3-bromo-5-[(dimethylamino)methyl]-4-hydroxybenzaldehyde | 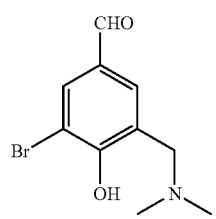 |
| 3-bromo-4-hydroxy-5-(pyrrolidin-1-ylmethyl)benzaldehyde | 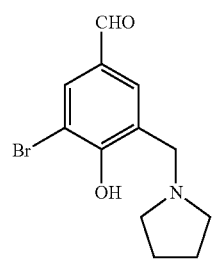 |
| 3-bromo-4-hydroxy-5-(piperidin-1-ylmethyl)benzaldehyde | 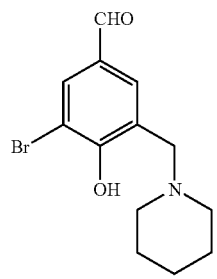 |

-continued
| | |
|---|---|
| 3-bromo-4-hydroxy-5-(morpholin-4-ylmethyl)benzaldehyde | 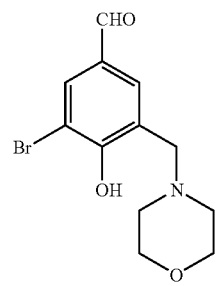 |
| 3-bromo-4-hydroxy-5-[(3-hydroxypyrrolidin-1-yl)methyl]-benzaldehyde | 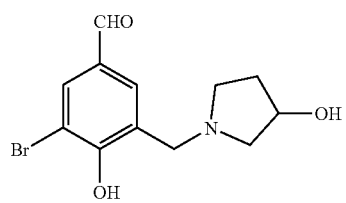 |
| 3-bromo-4-hydroxy-5-[(4-hydroxypiperidin-1-yl)methyl]benzaldehyde | 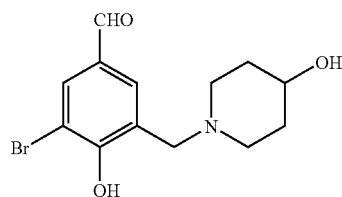 |
| 3-bromo-4-hydroxy-5-[(3-hydroxypiperidin-1-yl)methyl]benzaldehyde | 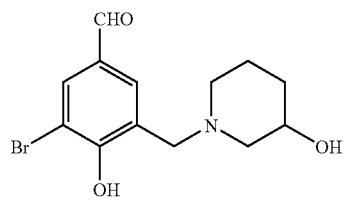 |
| 3-chloro-5-[(dimethylamino)methyl]-4-hydroxybenzaldehyde | 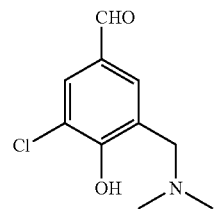 |
| 3-chloro-4-hydroxy-5-(pyrrolidin-1-ylmethyl)benzaldehyde | 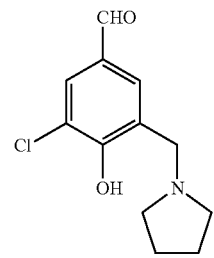 |

-continued
3-chloro-4-hydroxy-5-(piperidin-1-ylmethyl)benzaldehyde
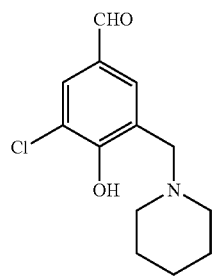
3-chloro-4-hydroxy-5-(morpholin-4-ylmethyl)benzaldehyde
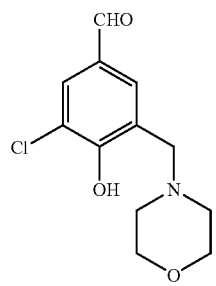
3-chloro-4-hydroxy-5-[(3-hydroxypyrrolidin-1-yl)methyl]-benzaldehyde
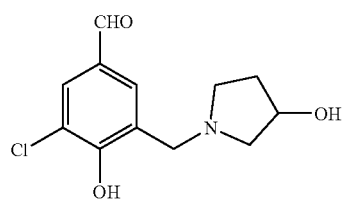
3-chloro-4-hydroxy-5-[(4-hydroxypiperidin-1-yl)methyl]benzaldehyde
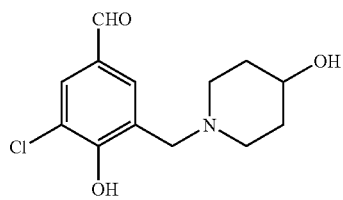
3-chloro-4-hydroxy-5-[(3-hydroxypiperidin-1-yl)methyl]benzaldehyde
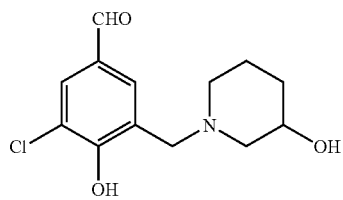
3-[(dimethylamino)methyl]-4-hydroxy-1-naphthaldehyde
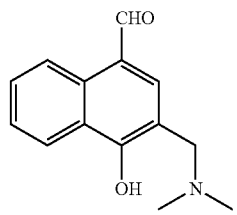

-continued
4-hydroxy-3-(pyrrolidin-1-ylmethyl)-1-naphthaldehyde
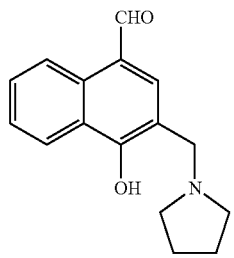
4-hydroxy-3-(piperidin-1-ylmethyl)-1-naphthaldehyde
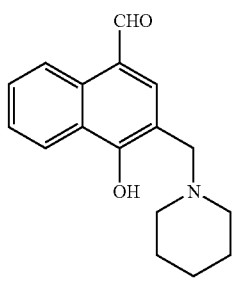
4-hydroxy-3-(morpholin-4-ylmethyl)-1-naphthaldehyde
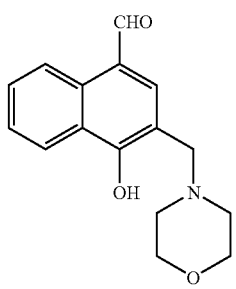
4-hydroxy-3-[(3-hydroxypyrrolidin-1-yl)methyl]-1-naphthaldehyde
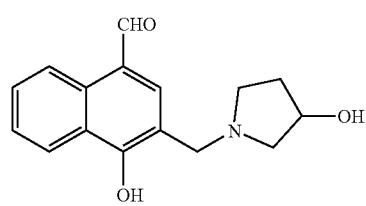
4-hydroxy-3-[(4-hydroxypiperidin-1-yl)methyl]-1-naphthaldehyde
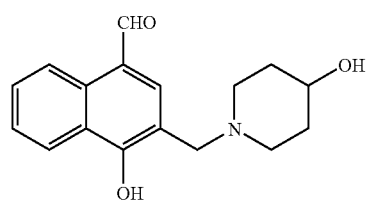
4-hydroxy-3-[(3-hydroxypiperidin-1-yl)methyl]-1-naphthaldehyde
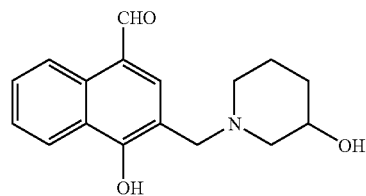

-continued
| | |
|---|---|
| 5-[(dimethylamino)methyl]-2,3,4-trihydroxybenzaldehyde | 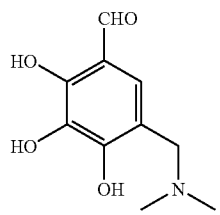 |
| 2,3,4-trihydroxy-5-(pyrrolidin-1-ylmethyl)benzaldehyde | 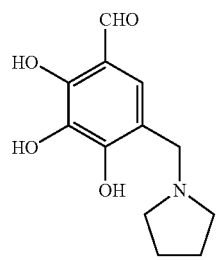 |
| 2,3,4-trihydroxy-5-(piperidin-1-ylmethyl)benzaldehyde | 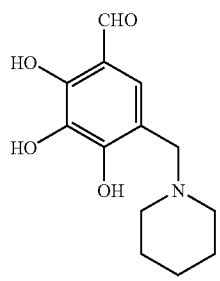 |
| 2,3,4-trihydroxy-5-(morpholin-4-ylmethyl)benzaldehyde | 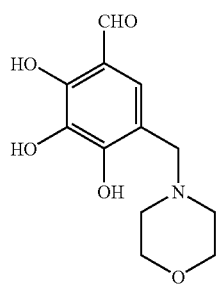 |
| 3-[(dimethylamino)methyl]-2,4,5-trihydroxybenzaldehyde | 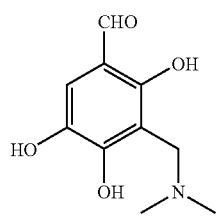 |
| 2,4,5-trihydroxy-3-(pyrrolidin-1-ylmethyl)benzaldehyde | 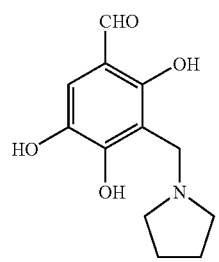 |

-continued

| 2,4,5-trihydroxy-3-(piperidin-1-ylmethyl)benz-aldehyde | 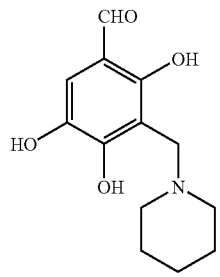 |
|---|---|
| 2,4,5-trihydroxy-3-(morpholin-4-ylmethyl)benz-aldehyde | 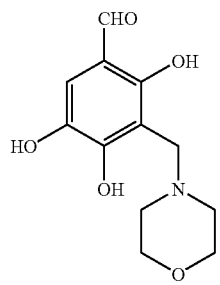 |

Moreover, the above-identified compounds may also be used as component A according to the formula (I) in which the carbonyl group of the —CHO group in formula (I) is derivatized or masked in such a manner that the reactivity of the carbon atom of the derivatized carbonyl group towards the component B CH-acidic compounds is always present. These derivatives are preferably addition compounds of:

a) amines and the derivatives thereof resulting in the formation of imines or oximes as an addition compound;
b) alcohols resulting in the formation of acetals as an addition compound; or
c) water resulting in the formation of hydrates as an addition compound onto the carbon atom of the formyl group —CHO in compounds according to the formula (I).

Compounds generally regarded as component B CH-acidic compounds are those which bear a hydrogen atom attached to an aliphatic carbon atom, activation of the corresponding carbon-hydrogen bond being brought about on the basis of electron-attracting substituents. In principle, no limits are set to selection of the CH-acidic compounds, providing that, after aldol condensation with the benzaldehyde derivatives according to the invention of the formula (I), a colored compound visible to the human eye is obtained. According to the invention preference is given to those CH-acidic compounds which contain an aromatic and/or a heterocyclic residue. The heterocyclic residue may in turn be aliphatic or aromatic.

Preferably, the compounds of the formula (I) are combined with at least one CH-acidic compound, which is selected from the formulae (II) or the enamine form thereof and/or (III)

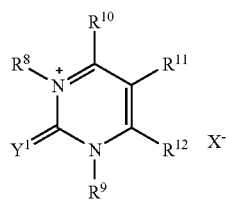
(II)

-continued

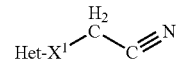
(III)

in which $R^8$ and $R^9$ mutually independently denote a linear or cyclic $C_1$-$C_6$ alkyl group, a $C_2$-$C_6$ alkenyl group, an optionally substituted aryl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$-alkoxy-$C_1$-$C_6$-alkyl group, an $R^{IV}R^{V}N$—$(CH_2)_p$— group, in which $R^{IV}$ and $R^V$ mutually independently denote a hydrogen atom, a $C_1$-$C_4$ alkyl group, a $C_1$-$C_4$ hydroxyalkyl group or an aryl-$C_1$-$C_6$-alkyl group, $R^{IV}$ and $R^V$, together with the nitrogen atom, being capable of forming a 5-, 6- or 7-membered ring and p denoting a number 2, 3, 4, 5 or 6;

$R^{10}$ and $R^{12}$ mutually independently denote a hydrogen atom or a $C_1$-$C_6$ alkyl group, at least one of the residues $R^{10}$ and $R^{12}$ meaning a $C_1$-$C_6$ alkyl group;

$R^{11}$ denotes a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, an $R^{VI}R^{VII}N$—$(CH_2)_q$— group, in which $R^{VI}$ and $R^{VII}$ mutually independently denote a hydrogen atom, a $C_1$-$C_6$ alkyl group, a $C_1$-$C_6$ hydroxyalkyl group or an aryl-$C_1$-$C_6$ alkyl group, and q denotes a number 1, 2, 3, 4, 5 or 6, the residue $R^{11}$ being capable of forming, together with one of the residues $R^{10}$ or $R^{12}$, a 5- or 6-membered aromatic ring, which may optionally be substituted with a halogen atom, a ($C_1$-$C_6$) alkyl group, a $C_1$-$C_6$ hydroxyalkyl group, a $C_2$-$C_6$ polyhydroxyalkyl group, a ($C_1$-$C_6$) alkoxy group, a $C_1$-$C_6$ hydroxyalkoxy group, a nitro group, a hydroxy group, an $R^{VIII}R^{IX}N$—$(CH_2)_s$— group, in which $R^{VIII}$ and $R^{IX}$ mutually independently denote a hydrogen atom, a $C_1$-$C_6$ alkyl group, a $C_1$-$C_6$ hydroxyalkyl group or an aryl-$C_1$-$C_6$-alkyl group, and s denotes a number 0, 1, 2, 3, 4, 5 or 6;

$Y^1$ denotes an oxygen atom, a sulfur atom or an $NR^X$ group, in which $R^X$ denotes a hydrogen atom, an aryl group, a heteroaryl group, a $C_1$-$C_6$ alkyl group or a $C_1$-$C_6$ arylalkyl group;

$X^-$ denotes a physiologically acceptable anion;

Het denotes an optionally substituted heteroaromatic; and $X^1$ denotes a direct bond or a carbonyl group.

The enamine forms of the compounds of the formula II have an equivalent action. The 1,2-dihydropyrimidinium derivatives according to the formula II are CH-acidic compounds. They are present in chemical equilibrium with the enamine form of the 1,2-dihydropyrimidinium derivatives according to the formula IIa. With the assistance of a base, it is possible in targeted manner to prepare the corresponding enamines from the compounds according to the formula II by deprotonation on the α-carbon atom of the $C_1$-$C_6$ alkyl residues $R^{10}$ or $R^{12}$. By way of example, this deprotonation is illustrated below, $R^{10}$ having been selected for clarification as the residue R—$CH_2$. A compound according to the formula IIa is an example of a enamine form of the 1,2-dihydropyrimidinium derivatives.

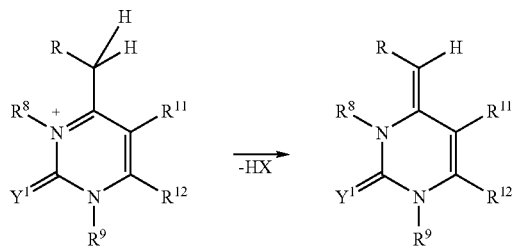

(IIa)

At least one group $R^{10}$ or $R^{12}$ according to the formula II mandatorily denotes a $C_1$-$C_6$ alkyl group. This alkyl group preferably bears at least two hydrogen atoms on its α-carbon atom. Particularly preferred alkyl groups are the methyl, ethyl, propyl, n-butyl, iso-butyl, n-pentyl, neopentyl, and n-hexyl group. $R^{10}$ and $R^{12}$ preferably mutually independently denote hydrogen or a methyl group, at least one group $R^{10}$ or $R^{12}$ meaning a methyl group.

In a preferred embodiment, $Y^1$ denotes an oxygen or a sulfur atom, more preferably an oxygen atom.

The residue $R^8$ is preferably selected from a ($C_1$-$C_6$) alkyl group (more preferably a methyl group), a $C_2$-$C_6$ alkenyl group (in particular an allyl group), a hydroxy-($C_2$ to $C_6$)-alkyl group or an optionally substituted benzyl group.

$R^{11}$ preferably denotes a hydrogen atom.

In a preferred embodiment, the residues $R^9$, $R^{10}$ and $R^{12}$ denote a methyl group, the residue $R^{11}$ a hydrogen atom, $Y^1$ an oxygen or a sulfur atom and the residue $R^8$ is selected from a ($C_1$-$C_6$) alkyl group (preferably a methyl group), a $C_2$-$C_6$ alkenyl group (in particular an allyl group), a hydroxy-($C_2$ to $C_6$)-alkyl group or an optionally substituted benzyl group.

The compounds according to the formula II are preferably selected from one or more compounds of the group of salts with a physiologically acceptable counterion $X^-$, which is formed of:

1,2-dihydro-1,3,4,6-tetramethyl-2-oxopyrimidinium;
1,2-dihydro-1,3-diethyl-4,6-dimethyl-2-oxopyrimidinium;
1,2-dihydro-1,3-dipropyl-4,6-dimethyl-2-oxopyrimidinium;
1,2-dihydro-1,3-di(2-hydroxyethyl)-4,6-dimethyl-2-oxopyrimidinium;
1,2-dihydro-1,3-diphenyl-4,6-dimethyl-2-oxopyrimidinium;
1,2-dihydro-1,3,4-trimethyl-2-oxopyrimidinium;
1,2-dihydro-1,3-diethyl-4-methyl-2-oxopyrimidinium;
1,2-dihydro-1,3-dipropyl-4-methyl-2-oxopyrimidinium;
1,2-dihydro-1,3-di(2-hydroxyethyl)-4-methyl-2-oxopyrimidinium;
1,2-dihydro-1,3-diphenyl-4-methyl-2-oxopyrimidinium;
1-allyl-1,2-dihydro-3,4,6-trimethyl-2-oxopyrimidinium;
1,2-dihydro-1-(2-hydroxyethyl)-3,4,6-trimethyl-2-oxopyrimidinium;
1,2-dihydro-1,3,4,6-tetramethyl-2-thioxopyrimidinium;
1,2-dihydro-1,3-diethyl-4,6-dimethyl-2-thioxopyrimidinium;
1,2-dihydro-1,3-dipropyl-4,6-dimethyl-2-thioxopyrimidinium;
1,2-dihydro-1,3-di(2-hydroxyethyl)-4,6-dimethyl-2-thioxopyrimidinium;
1,2-dihydro-1,3-diphenyl-4,6-dimethyl-2-thioxopyrimidinium;
1,2-dihydro-1,3,4-trimethyl-2-thioxopyrimidinium;
1,2-dihydro-1,3-diethyl-4-methyl-2-thioxopyrimidinium;
1,2-dihydro-1,3-dipropyl-4-methyl-2-thioxopyrimidinium;
1,2-dihydro-1,3-di(2-hydroxyethyl)-4-methyl-2-thioxopyrimidinium;
1,2-dihydro-1,3-diphenyl-4-methyl-2-thioxopyrimidinium;
1,2-dihydro-3,4-dimethyl-2-oxoquinazolinium; and
1,2-dihydro-3,4-dimethyl-2-thioxoquinazolinium.

Very particularly preferred compounds according to the formula II are selected from one or more compounds of the group of salts with a physiologically acceptable counterion $X^-$, which is formed of salts of:

1,2-dihydro-1,3,4,6-tetramethyl-2-oxopyrimidinium;
1,2-dihydro-1,3,4-trimethyl-2-oxopyrimidinium;
1-allyl-1,2-dihydro-3,4,6-trimethyl-2-oxopyrimidinium;
1,2-dihydro-1-(2-hydroxyethyl)-3,4,6-trimethyl-2-oxopyrimidinium; and
1,2-dihydro-1,3,4,6-tetramethyl-2-thioxopyrimidinium.

$X^-$ in the formula (II) as well as in the above lists preferably denotes halide, benzenesulfonate, p-toluenesulfonate, $C_1$ to $C_4$ alkanesulfonate, trifluoromethanesulfonate, perchlorate, 0.5 sulfate, hydrogensulfate, tetrafluoroborate, hexafluorophosphate or tetrachlorozincate. The anions chloride, bromide, iodide, hydrogensulfate or p-toluenesulfonate are particularly preferably used as $X^-$.

The residue Het according to the formula (III) preferably denotes the molecular fragment of the formula (IV),

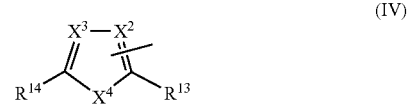

(IV)

in which $R^{13}$ and $R^{14}$ mutually independently denote a hydrogen atom, a hydroxy group, a halogen atom, a nitro group, a linear or cyclic $C_1$-$C_6$ alkyl group, a $C_2$-$C_6$ alkenyl group, an optionally substituted aryl group, a cyanomethyl group, a cyanomethylcarbonyl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$ alkoxy group, a $C_1$-$C_6$ alkoxycarbonyl group, a $C_1$-$C_6$-alkoxy-$C_2$-$C_6$-alkyl group, a $C_1$-$C_6$ sulfoalkyl group, a $C_1$-$C_6$ carboxyalkyl group, an $R^{XI}R^{XII}N$—$(CH_2)_r$— group, in which $R^{XI}$ and $R^{XIII}$ mutually independently denote a hydrogen atom, a linear or cyclic $C_1$-$C_6$ alkyl group, a $C_2$-$C_6$ alkenyl group, a $C_1$-$C_6$ hydroxyalkyl group or an aryl-$C_1$-$C_4$-alkyl group, $R^{XI}$ and $R^{XII}$, together with the nitrogen atom, being capable of forming a 5-, 6- or 7-membered ring and r denoting a number 0, 1, 2, 3 or 4, $R^{13}$ and/or $R^{14}$ being capable of forming an optionally substituted aromatic or heteroaromatic 5- or 6-membered ring fused to the ring of the remainder of the molecule;

$X^2$ and $X^3$ mutually independently denote a nitrogen atom or a $CR^{15}$ group, $R^{15}$ denoting a hydrogen atom, a hydroxy group, a halogen atom, a nitro group, a linear or cyclic $C_1$-$C_6$ alkyl group, a $C_2$-$C_6$ alkenyl group, an optionally substituted aryl group, a cyanomethyl group, a cyanomethylcarbonyl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$ alkoxy group, a $C_1$-$C_6$ alkoxycarbonyl group, a $C_1$-$C_6$-alkoxy-$C_2$-$C_6$-alkyl group, a $C_1$-$C_6$ sulfoalkyl group, a $C_1$-$C_6$ carboxyalkyl group, and an $R^{XIII}R^{XIV}N$—$(CH_2)_t$ group, in which $R^{XIII}$ and $R^{XIV}$ mutually independently denote a hydrogen atom, a linear or cyclic $C_1$-$C_6$ alkyl group, a $C_2$-$C_6$ alkenyl group, a $C_1$-$C_6$ hydroxyalkyl group or an aryl-$C_1$-$C_6$-alkyl group, $R^{XIII}$ and $R^{XIV}$, together with the nitrogen atom, being capable of forming a 5-, 6- or 7-membered ring and t denoting a number 0, 1, 2, 3 or 4, at least one of the substituents $X^2$ and $X^3$, together with the remainder of the molecule, being capable of forming a fused, optionally substituted aromatic 5- or 6-membered ring; and $X^4$ denotes an oxygen atom, a sulfur atom, a vinylene group or an N—H group, the latter two stated groups mutually independently optionally being capable of substitution with a linear or cyclic $C_1$-$C_6$ alkyl group, a $C_2$-$C_6$ alkenyl group, an optionally substituted aryl group, an optionally substituted heteroaryl group, an aryl-$C_1$-$C_6$-alkyl group, a $C_2$-$C_6$ hydroxyalkyl group, a $C_2$-$C_6$ polyhydroxyalkyl group, a $C_1$-$C_6$-alkoxy-$C_2$-$C_6$-alkyl group, a $C_1$-$C_6$ sulfoalkyl group, a $C_1$-$C_6$ carboxyalkyl group, an $R^{XV}R^{XVI}N$—$(CH_2)_u$—, in which $R^{XV}$ and $R^{XVI}$ mutually independently denote a hydrogen atom, a linear or cyclic $C_1$-$C_6$ alkyl group, a $C_1$-$C_6$ alkenyl group, a $C_1$-$C_6$ hydroxyalkyl group or an aryl-$C_1$-$C_4$-alkyl group, $R^{XV}$ and $R^{XVI}$, together with the nitrogen atom, being capable of forming a 5-, 6- or 7-membered ring and u denoting a number 0, 1, 2, 3 or 4, with the proviso that, if $X^4$ denotes a vinylene group, at least one of the groups $X^2$ or $X^3$ means a nitrogen atom.

In an exemplary embodiment, attachment of the heterocyclic ring according to the formula (IV) to the molecular fragment —$X^1$—$CH_2$—$C\equiv N$, so obtaining the compound according to the formula (III), is made to the ring of the heterocycle and replaces a hydrogen atom attached to said ring. Consequently, the substituents $R^{13}$, $R^{14}$, $X^2$, $X^3$ and $X^3$ and $X^4$ are selected such that at least one of these substituents permits the formation of such a bond. In turn at least one of the residues $R^{13}$ or $R^{14}$ form the bond to the molecular fragment —$X^1$—$CH_2$—$C\equiv N$, if $X^4$ is an oxygen atom or a sulfur atom and $X^2$ and $X^3$ mean a nitrogen atom.

In a preferred embodiment, the residue Het according to the formula (IV) is derived from the heteroaromatics furan, thiophene, pyrrole, isoxazole, isothiazole, imidazole, oxazole, thiazole, pyridine, pyridazine, pyrimidine, pyrazine, 1,2,3-triazine, 1,2,4-triazine, 1,3,5-triazine, benzopyrrole, benzofuran, benzothiophene, benzimidazole, benzoxazole, indazole, benzoisoxazole, benzoisothiazole, indole, quinoline, isoquinoline, cinnoline, phthalazine, quinazoline, quinoxaline, acridine, benzoquinoline, benzoisoquinoline, benzothiazole, phenazine, benzocinnoline, benzoquinazoline, benzoquinoxaline, phenoxazine, phenothiazine, nephthyridine, phenanthroline, indolizine, quinolizine, carboline, purine, pteridine and coumarin, the above-stated heteroaromatics possibly being substituted with at least one group selected from a halogen atom, a nitro group, a thio group, a thio-($C_1$-$C_6$)-alkyl group, a heteroaryl group, an aryl group, a ($C_1$-$C_6$) alkyl group, a ($C_1$-$C_6$) alkoxy group, a hydroxy group, a ($C_2$-$C_6$) hydroxyalkyl group, a ($C_2$-$C_6$) polyhydroxyalkyl group, a ($C_1$-$C_6$)-alkoxyl-($C_1$-$C_6$)-alkyl group, an aryl-($C_1$-$C_6$)-alkyl group, an amino group, a ($C_1$-$C_6$) monoalkylamino group, a ($C_1$-$C_6$) dialkylamino group, a dialkylaminoalkyl group —$(CH_2)_n$—NR'R'', in which n is an integer of 2 and 6 and R' and R'' mutually independently mean a linear or branched alkyl group, which may optionally together form a ring.

The compounds according to the formula (III) are preferably selected from the group consisting of 2-(2-furoyl)-acetonitrile, 2-(5-bromo-2-furoyl)-acetonitrile, 2-(5-methyl-2-trifluoromethyl-3-furoyl)-acetonitrile, 3-(2,5-dimethyl-3-furyl)-3-oxopropanenitrile, 2-(2-thenoyl)-acetonitrile, 2-(3-thenoyl)-acetonitrile, 2-(5-fluoro-2-thenoyl)-acetonitrile, 2-(5-chloro-2-thenoyl)-acetonitrile, 2-(5-bromo-2-thenoyl)-acetonitrile, 2-(5-methyl-2-thenoyl)-acetonitrile, 2-(2,5-dimethylpyrrol-3-oyl)-acetonitrile, 2-(1,2,5-trimethylpyrrol-3-oyl)-acetonitrile, 1H-benzimidazol-2-ylacetonitrile, 1H-benzothiazol-2-ylacetonitrile, 2-(pyrid-2-yl)-acetonitrile, 2,6-bis(cyanomethyl)-pyridine, 2-(indol-3-oyl)-acetonitrile, 2-(2-methylindol-3-oyl)-acetonitrile, 8-cyanoacetyl-7-methoxy-4-methylcoumarin, 2-(2-isopropyl-5,6-benzoquinolin-4-oyl)-acetonitrile, 2-(2-phenyl-5,6-benzoquinolin-4-oyl)-acetonitrile, 2-(quinoxalin-2-yl)-acetonitrile, 2-(coumaron-2-yl)-acetonitrile, 6,7-dichloro-5-(cyanoacetyl)-2,3-dihydro-1-benzofuran-2-carboxylic acid tert.-butyl ester, 2-(6-hydroxy-4,7-dimethoxy-1-benzofuran-5-oyl)-acetonitrile and 2-(1-phenyl-1,4-dihydrothiochromeno[4,3c]pyrazol-3-oyl)-acetonitrile. 1H-benzimidazol-2-ylacetonitrile[2-(cyanomethyl)benzimidazole] is particularly preferred.

In a preferred embodiment, the component B CH-acidic compounds comprise at least one compound of the group which is formed from salts with a physiologically acceptable counterion $X^-$:

of 1,2-dihydro-1,3,4,6-tetramethyl-2-oxopyrimidinium;
of 1,2-dihydro-1,3,4-trimethyl-2-oxopyrimidinium;
of 1-allyl-1,2-dihydro-3,4,6-trimethyl-2-oxopyrimidinium;
of 1,2-dihydro-1-(2-hydroxyethyl)-3,4,6-trimethyl-2-oxopyrimidinium;
of 1,2-dihydro-1,3,4,6-tetramethyl-2-thioxopyrimidinium; and
1H-benzimidazole-2-ylacetonitrile[2-(cyanomethyl)benzimidazole].

In a further embodiment, to extend the color spectrum it may be advantageous to add at least one further compound as component C to the agents, in addition to at least one compound according to the formula (I) as component A and at least one compound of the component B. The component C compound is selected from at least one reactive carbonyl compound other than compounds of the formula (I).

In an exemplary embodiment, reactive carbonyl compounds as component C have at least one carbonyl group as a reactive group, which reacts with the CH-acidic compound according to component B to form a carbon-carbon bond. Preferred reactive carbonyl compounds are aldehydes and ketones, in particular aromatic aldehydes. Furthermore, in another exemplary embodiment, component C also includes those compounds in which the reactive carbonyl group is derivatized or masked in such a manner that the reactivity of the carbon atom of the derivatized carbonyl group towards the component B CH-acidic compounds is always present. These derivatives are preferably addition compounds of:

a) amines and the derivatives thereof resulting in the formation of imines or oximes as an addition compound;
b) alcohols resulting in the formation of acetals or ketals as an addition compound; or
c) water resulting in the formation of hydrates as an addition compound (component C is derived in this case c) from an aldehyde)

onto the carbon atom of carbonyl group of the reactive carbonyl compound.

Preferred component C reactive carbonyl compounds are selected from the group consisting of benzaldehyde and the derivatives thereof, naphthaldehyde and the derivatives thereof, cinnamaldehyde and the derivatives thereof, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischer's aldehyde or tribasic aldehyde), 2-indolealdehyde, 3-indolealdehyde, 1-methylindole-3-aldehyde, 2-methylindole-3-aldehyde, 2-(1,3',3'-trimethyl-2-indolinylidene)-acetaldehyde, 1-methylpyrrole-2-aldehyde, 4-pyridinealdehyde, 2-pyridinealdehyde, 3-pyridinealdehyde, pyridoxal, antipyrine-4-aldehyde, furfural, 5-nitrofurfural, 2-thenoyltrifluoroacetone, chromone-3-aldehyde, 3-(5'-nitro-2'-furyl)-acrolein, 3-(2'-furyl)-acrolein and imidazole-2-aldehyde, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 5-(4-dimethylamino-1-naphthyl)penta-3,5-dienal, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium benzene sulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxylsatin, quinisatin, and 1-methylquinisatin, as well as any desired mixtures of the above-stated compounds.

Benzaldehyde, cinnamaldehyde, and naphthaldehyde as well as the derivatives thereof, in particular with one or more hydroxy, alkoxy or amino substituents are very particularly preferably used in the agents as the component C reactive carbonyl compound. Compounds according to the formula (Ca-1) which are in turn here preferred are those,

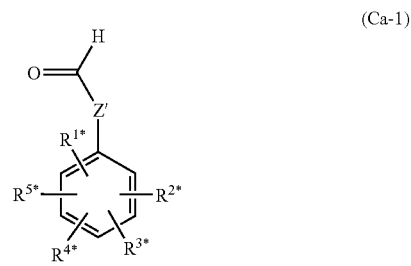

(Ca-1)

in which:

$R^{1*}$ and $R^{2*}$ and $R^{3*}$ mutually independently denote a hydrogen atom, a halogen atom, a $C_1$-$C_6$ alkyl group, a ($C_2$ to $C_6$) alkenyl group, a hydroxy group, a $C_1$-$C_6$ alkoxy group, a $C_1$-$C_6$ dialkylamino group, a di($C_2$-$C_6$ hydroxyalkyl)amino group, a di($C_1$-$C_6$-alkoxy-$C_1$-$C_6$-alkyl)amino group, a $C_1$-$C_6$ hydroxyalkyloxy group, a sulfonyl group, a carboxy group, a sulfonic acid group, a sulfonamido group, a sulfonamide group, carbamoyl group, a $C_2$-$C_6$ acyl group or a nitro group;

Z' denotes a direct bond or a vinylene group; and $R^{4*}$ and $R^{5*}$ denote a hydrogen atom or together form, with the remainder of the molecule, a 5- or 6-membered aromatic or aliphatic ring.

The benzaldehyde, naphthaldehyde or cinnamaldehyde derivatives of the carbonyl compound according to component C are particularly preferably selected from at least one compound of the group comprising:

4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methoxybenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-di-iodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 3-hydroxy-4-nitrobenzaldehyde, 2-hydroxy-3-methoxy-5-nitrobenzaldehyde, 5-nitrovanillin, 2,5-dinitrosalicylaldehyde, 5-bromo-3-nitrosalicylaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 3-allyl-4-hydroxybenzaldehyde, 3-allyl-4-hydroxy-5-methoxybenzaldehyde, 3-allyl-4-hydroxy-5-methylbenzaldehyde, 3-allyl-5-bromo-4-hydroxybenzaldehyde, 3,5-diallyl-4-hydroxybenzaldehyde, 3-allyl-4-hydroxy-5-formylbenzaldehyde (5-allyl-4-hydroxyisophthalaldehyde) and piperonal. These compounds are also at the same time particularly preferred representatives of component C, at least one of which may be contained as component C in the agents contemplated herein.

In a further embodiment the dyeing agent additionally contains at least one reaction product (hereinafter known as reaction product RP) from a compound of the formula I and a component B compound as a direct dye. Such reaction products RP may for example be obtained by heating the two reactants in an aqueous neutral to weakly alkaline medium, the reaction products RP being either precipitated as a solid from the solution or isolated therefrom by evaporation of the solution. It is additionally possible to produce the reaction products in a manner similar to the method described in the literature in K. Z. Gadella et al., Bulletin of the National Research Centre (Egypt), 1993, 18(3), 151-162 or H. Baumann et al, *J. Liebigs Ann. Chem.*, 1968, 717, 124-136.

For synthesis of the reaction products RP, molar ratios of component B to the compound according to the formula I of approximately 1:1 to approximately 1:2 may be advisable.

Particularly preferred reaction products RP are selected from compounds of the formulae (V), (VI) and/or (VII),

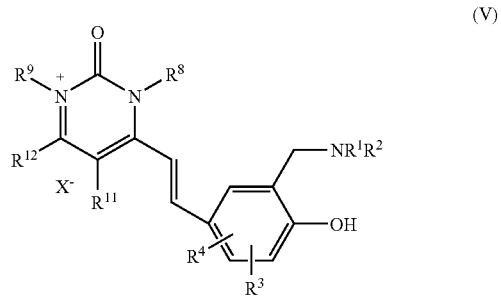

(V)

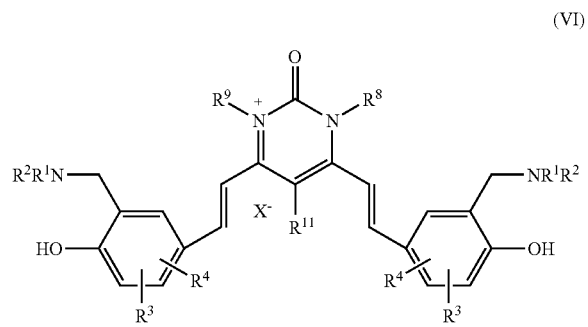

(VI)

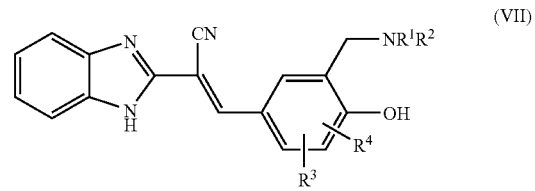

(VII)

in which the residues $R^1$, $R^2$, $R^3$, $R^4$, $R^8$, $R^9$, $R^{11}$, $R^{12}$ and $X^-$ are defined as in the formulae (I) and (II). In formula (V) $R^{12}$ preferably denotes a hydrogen atom or a methyl group. It is particularly preferable if, according to the formulae (V) and (VI), $R^{11}$ denotes a hydrogen atom.

For the residues $R^1$, $R^2$, $R^3$, $R^4$, $R^8$, $R^9$, $R^{11}$, $R^{12}$ and $X^-$ the definitions stated under the further embodiments of formulae (I) and (II) also apply.

In an exemplary embodiment, the above-stated compounds of the formula I, the component B, component C compounds and the reaction products RP, if used, are in each case used in a quantity of from about 0.03 to about 65 mmol, in preferably of from about 1 to about 40 mmol, relative to 100 g of the total dyeing agent.

Additionally, the agents may contain at least one developer component and optionally at least one coupler component as oxidation dye precursors.

In an exemplary embodiment, it is preferred to use a p-phenylenediamine derivative or one of the physiologically acceptable salts thereof as the developer component. Particularly preferred p-phenylenediamine derivatives are those of the formula (E1)

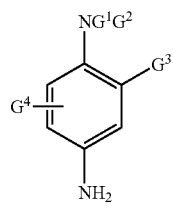

(E1)

wherein

G1 denotes a hydrogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$)-alkoxy-($C_1$ to $C_4$)-alkyl residue, a 4'-aminophenyl residue or a ($C_1$ to $C_4$) alkyl residue, which is substituted with a nitrogenous group, a phenyl or a 4'-aminophenyl residue;

$G^2$ denotes a hydrogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$)-alkoxy-($C_1$ to $C_4$)-alkyl residue or a ($C_1$ to $C_4$) alkyl residue, which is substituted with a nitrogenous group;

$G^3$ denotes a hydrogen atom, a halogen atom, such as a chlorine, bromine, iodine or fluorine atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$) hydroxyalkoxy residue, a ($C_1$ to $C_4$) acetylaminoalkoxy residue, a mesylamino-$C_1$ to $C_4$-alkoxy residue or a $C_1$ to $C_4$ carbamoylaminoalkoxy residue;

$G^4$ denotes a hydrogen atom, a halogen atom or a $C_1$ to $C_4$ alkyl residue or if $G^3$ and $G^4$ are in ortho position relative to one another, they may together form a bridging α,ω-alkylenedioxo group, such as for example an ethylenedioxy group.

Particularly preferred p-phenylenediamines of the formula (E1) are selected from one or more compounds of the group which is formed from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(β-hydroxyethyl)-p-phenylenediamine, 4-N,N-bis-(β-hydroxyethyl)amino-2-methylaniline, 4-N,N-bis-(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyl)-p-phenylenediamine, 2-(β-acetylaminoethyloxy)-p-phenylenediamine, N-(β-methoxyethyl)-p-phenylenediamine, N-(4-amino-3-methylphenyl)-N-[3-(1H-imidazol-1-yl)propyl]amine, 5,8-diaminobenzo-1,4-dioxane and the physiologically acceptable salts thereof.

p-Phenylenediamine derivatives of the formula (E1) which are very particularly preferred are selected from at least one compound of the group comprising p-phenylenediamine, p-tolylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, N-(4-amino-3-methylphenyl)-N-[3-(1H-imidazol-1-yl)propyl]amine, and the physiologically acceptable salts of these compounds.

It may furthermore be preferred to use compounds which contain at least two aromatic nuclei which are substituted with amino and/or hydroxyl groups as the developer component.

Among binuclear developer components which may be used in the dye compositions, mention may in particular be made of the compounds which correspond to the following formula (E2) and the physiologically acceptable salts thereof,

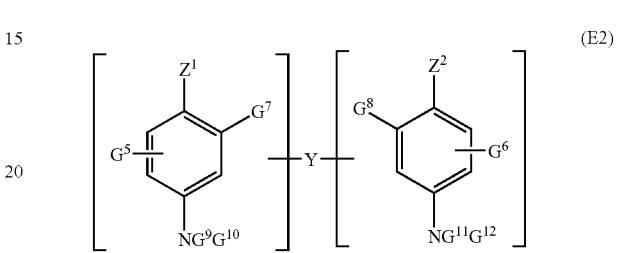

(E2)

wherein:

$Z^1$ and $Z^2$ mutually independently denote a hydroxyl or $NH_2$ residue, which is optionally substituted by a $C_1$ to $C_4$ alkyl residue, by a $C_1$ to $C_4$ hydroxyalkyl residue and/or by a bridging member Y or which is optionally part of a bridging ring system;

the bridging member Y denotes an alkylene group with 1 to 14 carbon atoms, such as for example a linear or branched alkylene chain or an alkylene ring which may be interrupted or terminated by one or more nitrogenous groups and/or one or more heteroatoms such as oxygen, sulfur or nitrogen atoms and may optionally be substituted by one or more hydroxyl or $C_1$ to $C_8$ alkoxy residues or a direct bond;

$G^5$ and $G^6$ mutually independently denote a hydrogen or halogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$) aminoalkyl residue or a direct compound for bridging member Y; and $G^7$, $G^8$, $G^9$, $G^{10}$, $G^{11}$ and $G^{12}$ mutually independently denote a hydrogen atom, a direct bond to the bridging member Y or a $C_1$ to $C_4$ alkyl residue, with the proviso that the compounds of the formula (E2) contain only one bridging member Y per molecule.

The substituents used in formula (E2) are defined herein in a manner similar to the above explanations.

Preferred binuclear developer components of the formula (E2) are selected in particular from at least one of the following compounds: N,N'-bis-(β-hydroxyethyl)-N,N'-bis-(4'-aminophenyl)-1,3-diaminopropan-2-ol, N,N'-bis-(β-hydroxyethyl)-N,N'-bis-(4'-aminophenyl)-ethylenediamine, N,N'-bis-(4-aminophenyl)-tetramethylenediamine, N,N'-bis-(β-hydroxyethyl)-N,N'-bis-(4'-aminophenyl-tetramethylenediamine, N,N'-bis-(4-(methylamino)phenyl)-tetramethylenediamine, N,N'-diethyl-N,N'-bis-(4'-amino-3'-methylphenyl)-ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl) piperazine, N-(4'-aminophenyl)-p-phenylenediamine and 1,10-bis-(2',5'-diaminophenyl)-1,4,7,10-tetraoxadecane and the physiologically acceptable salts thereof.

In a preferred embodiment, binuclear developer components of the formula (E2) are selected from N,N'-bis-(β-hydroxyethyl)-N,N'-bis-(4'-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane or one of the physiologically acceptable salts of these compounds.

In another preferred embodiment, a p-aminophenol derivative or one of the physiologically acceptable salts thereof is used as the developer component. Particular preference is given to p-aminophenol derivatives of the formula (E3)

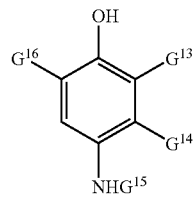

(E3)

wherein:
$G^{13}$ denotes a hydrogen atom, a halogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$)-alkoxy-($C_1$ to $C_4$)-alkyl residue, a $C_1$ to $C_4$ aminoalkyl residue, a hydroxy-($C_1$ to $C_4$)-alkylamino residue, a ($C_1$ to $C_4$) hydroxyalkoxy residue, a $C_1$ to $C_4$-hydroxyalkyl-($C_1$ to $C_4$)-aminoalkyl residue or a (di-$C_1$ to $C_4$-alkylamino)-($C_1$ to $C_4$)-alkyl residue;

$G^{14}$ denotes a hydrogen or halogen atom, a $C_1$ to $C_4$ alkyl residue, a $C_1$ to $C_4$ monohydroxyalkyl residue, a $C_2$ to $C_4$ polyhydroxyalkyl residue, a ($C_1$ to $C_4$)-alkoxy-($C_1$ to $C_4$)-alkyl residue, a $C_1$ to $C_4$ aminoalkyl residue or a $C_1$ to $C_4$ cyanoalkyl residue;

$G^{15}$ denotes hydrogen, a $C_1$ to $C_4$ alkyl residue, a $C_1$ to $C_4$ monohydroxyalkyl residue, a $C_2$ to $C_4$ polyhydroxyalkyl residue, a phenyl residue or a benzyl residue; and $G^{16}$ denotes hydrogen or a halogen atom.

The substituents used in formula (E3) are defined herein in a manner similar to the above explanations.

Preferred p-aminophenols of the formula (E3) are in particular p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenyl, 4-amino-2-chlorophenol, 4-amino-2,6-dichlorophenyl, 4-amino-2-(diethylaminomethyl)-phenol and the physiologically acceptable salts thereof.

More preferably, compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

The developer component may furthermore be selected from o-aminophenol and the derivatives thereof, such as for example 2-amino-4-methylphenol, 2-amino-5-methylphenol or 2-amino-4-chlorophenol.

The developer component may also be selected from heterocyclic developer components, such as for example pyrimidine derivatives, pyrazole derivatives, pyrazolopyrimidine derivatives or the physiologically acceptable salts thereof.

In a preferred embodiment, pyrimidine derivatives are selected from compounds according to the formula (E4) or the physiologically acceptable salts thereof

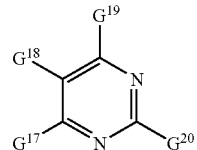

(E4)

in which:
$G^{17}$, $G^{18}$ and $G^{19}$ mutually independently denote a hydrogen atom, a hydroxy group, a ($C_1$ to $C_4$) alkoxy group or an amino group and $G^{20}$ denotes a hydroxyl group or an —$NG^{21}G^{22}$ group, in which $G^{21}$ and $G^{22}$ mutually independently denote a hydrogen atom, a ($C_1$ to $C_4$) alkyl group, a ($C_1$ to $C_4$) monohydroxyalkyl group, with the proviso that at most two of the groups from $G^{17}$, $G^{18}$, $G^{19}$ and $G^{20}$ mean a hydroxyl group and at most two of the residues $G^{17}$, $G^{18}$ and $G^{19}$ denote a hydrogen atom. It is in turn preferred if, according to the formula (E4), at least two groups from $G^{17}$, $G^{18}$, and $G^{19}$ and $G^{20}$ denote an —$NG^{21}G^{22}$ group and at most two groups from $G^{17}$, $G^{18}$, $G^{19}$ and $G^{20}$ denote a hydroxy group.

Particularly preferred pyrimidine derivatives include the compounds 2,4,5,6-tetraminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

In an exemplary embodiment, pyrazole derivatives are selected according to the invention from compounds according to the formula (E5),

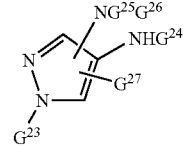

(E5)

in which
$G^{23}$, $G^{24}$, $G^{25}$ mutually independently denote a hydrogen atom, a ($C_1$ to $C_4$) alkyl group, a ($C_1$ to $C_4$) monohydroxyalkyl group, a ($C_2$ to $C_4$) polyhydroxyalkyl group, an optionally substituted aryl group or an optionally substituted aryl-($C_1$ to $C_4$)-alkyl group, with the proviso that, if $G^{25}$ denotes a hydrogen atom, $G^{26}$ may, in addition to the above-stated groups, additionally denote an —$NH_2$ group;

$G^{26}$ denotes a hydrogen atom, a ($C_1$ to $C_4$) alkyl group, a ($C_1$ to $C_4$) monohydroxyalkyl group or a ($C_2$ to $C_4$) polyhydroxyalkyl group; and $G^{27}$ denotes a hydrogen atom, an optionally substituted aryl group, a ($C_1$ to $C_4$) alkyl group or a ($C_1$ to $C_4$) monohydroxyalkyl group, in particular a hydrogen atom or a methyl group.

In the formula (E5) the residue —$NG^{25}G^{26}$ preferably binds to position 5 and the residue $G^{27}$ to position 4 of the pyrazole cycle.

Particularly preferred pyrazole derivatives include the compounds selected from: 4,5-diamino-1-methylpyrazole, 4,5-diamino-1-(β-hydroxyethyl)pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert.-butyl-1-methylpyrazole, 4,5-diamino-1-tert.-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(β-aminoethyl)amino-1,3-dimethylpyrazole, and the physiologically acceptable salts thereof.

Preferred pyrazolopyrimidine derivatives include the derivatives of the pyrazolo[1,5-a]pyrimidine of the following formula (E6) and the tautomeric forms thereof, where a tautomeric equilibrium prevails:

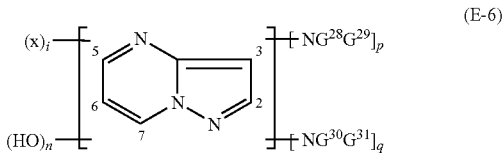

(E-6)

wherein:
$G^{28}$, $G^{29}$ and $G^{30}$, $G^{31}$ mutually independently denote a hydrogen atom, a $C_1$ to $C_4$ alkyl residue, an aryl residue, a $C_1$ to $C_4$ monohydroxyalkyl residue, a ($C_2$ to $C_4$) polyhydroxyalkyl residue, a ($C_1$ to $C_4$)-alkoxy-($C_1$ to $C_4$)-alkyl residue, a ($C_1$ to $C_4$) aminoalkyl residue, which may optionally be protected by an acetyl ureide or a sulfonyl residue, a ($C_1$ to $C_4$)-alkylamino-($C_1$ to $C_4$)-alkyl residue, a di-[($C_1$ to $C_4$)-alkyl]-($C_1$ to $C_4$)-aminoalkyl residue, the dialkyl residues optionally forming a carbocycle or a heterocycle with 5 or 6 chain links, a ($C_1$ to $C_4$) monohydroxyalkyl or a di[($C_1$ to $C_4$)-hydroxyalkyl]-($C_1$ to $C_4$)-aminoalkyl residue;

the X residues mutually independently denote a hydrogen atom, a $C_1$ to $C_4$ alkyl residue, an aryl residue, a $C_1$ to $C_4$ monohydroxyalkyl residue, a $C_2$ to $C_4$ polyhydroxyalkyl residue, a $C_1$ to $C_4$ aminoalkyl residue, a ($C_1$ to $C_4$)-alkylamino-($C_1$ to $C_4$)-alkyl residue, a di-[($C_1$ to $C_4$)-alkyl]-($C_1$ to $C_4$)-aminoalkyl residue, the dialkyl residues optionally forming a carbocycle or a heterocycle with 5 or 6 chain links, a ($C_1$ to $C_4$) hydroxyalkyl or a di-[($C_1$ to $C_4$)-hydroxyalkyl]amino-($C_1$ to $C_4$)-alkyl residue, an amino residue, a $C_1$ to $C_4$-alkyl or di-($C_1$ to $C_4$-hydroxyalkyl)amino residue, a halogen atom, a carboxylic acid group or a sulfonic acid group;

i has the value 0, 1, 2 or 3;
p has the value 0 or 1;
q has the value 0 or 1; and
n has the value 0 or 1, with the proviso that
the sum of p+q does not equal 0;
if p+q is equal to 2, n has the value 0, and the groups $NG^{28}G^{29}$ and $NG^{30}G^{31}$ occupy positions (2,3); (5,6); (6,7); (3,5) or (3,7); and
if p+q is equal to 1, n has the value 1, and the groups $NG^{28}G^{29}$ (or $NG^{30}G^{31}$) and the OH group occupy positions (2,3); (5,6); (6,7); (3,5) or (3,7).

The substituents used in formula (E6) are defined in a manner similar to the above explanations.

If the pyrazolo[1,5a]pyrimidine of the above-stated formula (E6) contains a hydroxy group in one of positions 2, 5 or 7 of the ring system, a tautomeric equilibrium prevails, which is shown for example in the following scheme:

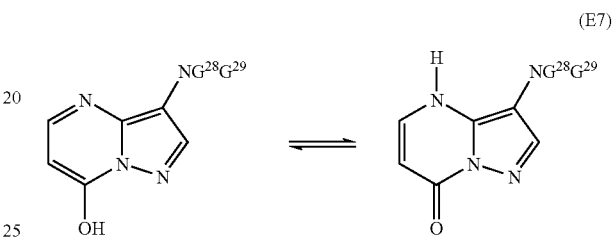

(E7)

Pyrazolo[1,5a]pyrimidines of the above-stated formula (E7) which may in particular be mentioned are:
pyrazolo[1,5a]pyrimidine-3,7-diamine;
2,5-dimethylpyrazolo[1,5-a]pyrimidine-3,7-diamine;
pyrazolo[1,5a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)-ethanol;
2-(7-aminopyrazolo[1,5-a]pyrimidin-3-ylamino)-ethanol;
2-[(3-aminopyrazolo[1,5-a]pyrimidin-7-yl)-(2-hydroxyethyl)amino]ethanol;
2-[(7-aminopyrazolo[1,5-a]pyrimidin-3-yl)-(2-hydroxyethyl)amino]ethanol;
5,6-dimethylpyrazolo[1,5-a]pyrimidine-3,7-diamine;
2,6-dimethylpyrazolo[1,5-a]pyrimidine-3,7-diamine;
3-amino-7-dimethylamino-2,5-dimethylpyrazolo[1,5-a]pyrimidine;

and the physiologically acceptable salts thereof and the tautomeric forms thereof, if a tautomeric equilibrium exists.

The pyrazolo[1,5-a]pyrimidines of the formula (E6) may be produced as described in the literature by cyclization starting from an aminopyrazole or from hydrazine.

Very particularly preferred developer components are selected from at least one compound from the group, which is formed from p-phenylenediamine, p-tolylenediamine, 2-(β-hydroxyethyl)-p-phenylenediamine, 2-(α,β-dihydroxyethyl)-p-phenylenediamine, N,N-bis-(β-hydroxyethyl)-p-phenylenediamine, N-(4-amino-3-methylphenyl)-N-[3-(1H-imidazol-1-yl)propyl]amine, N,N'-bis-(β-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(α,β-dihydroxyethyl)phenol and 4-amino-2-(diethylaminomethyl)phenol, 4,5-diamino-1-(β-hydroxyethyl)pyrazole, 2,4,5,6-tetraminopyrimidine, 4-hydroxy-2,5,6-triaminopyrimidine, 2-hydroxy-4,5,6-triaminopyrimidine, and the physiologically acceptable salts of these compounds.

Examples of the residues stated as substituents for the compounds of the formulae (E1) to (E6) are listed hereafter: examples of ($C_1$ to $C_4$) alkyl residues are the groups —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$. Examples of ($C_1$ to $C_4$) alkoxy residues are —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, in particular a methoxy or an ethoxy group.

Preferred examples of a ($C_1$ to $C_4$) monohydroxyalkyl group may furthermore be —$CH_2OH$, —$CH_2CH_2$—OH, —$CH_2CH_2CH_2$—OH, —$CHCH(OH)CH_3$, —$CH_2CH_2CH_2CH_2OH$, the group —$CH_2CH_2$—OH being preferred.

A particularly preferred example of a ($C_2$ to $C_4$) polyhydroxyalkyl group is the 1,2-dihydroxyethyl group.

Examples of halogen atoms are F, Cl or Br atoms, Cl atoms being very particularly preferred examples.

Examples of nitrogenous groups are in particular —$NH_2$, ($C_1$ to $C_4$) monoalkylamino groups, ($C_1$ to $C_4$) dialkylamino groups, ($C_1$ to $C_4$) trialkylammonium groups, ($C_1$ to $C_4$) monohydroxyalkylamino groups, imidazolinium and —$NH_3^+$.

Examples of ($C_1$ to $C_4$) monoalkylamino groups are —$NHCH_3$, —$NHCH_2CH_3$, —$NHCH_2CH_2CH_3$, and —$NHCH(CH_3)_2$.

Examples of ($C_1$ to $C_4$) dialkylamino group are —$N(CH_3)_2$, and —$N(CH_2CH_3)_2$.

Examples of ($C_1$ to $C_4$) trialkylammonium groups are —$N+(CH_3)_3$, —$N+(CH_3)_2(CH_2CH_3)$, and —$N+(CH_3)(CH_2CH_3)_2$.

Examples of ($C_1$ to $C_4$) hydroxyalkylamino residues are —NH—$CH_2CH_2$—OH, —NH—$CH_2CH_2OH$, —NH—$CH_2CH_2CH_2OH$, and —NH—$CH_2CH_2CH_2OH$.

Examples of ($C_1$ to $C_4$)-alkoxy-($C_1$ to $C_4$)-alkyl groups are the groups —$CH_2CH_2$—O—$CH_3$, —$CH_2CH_2CH_2$—O—$CH_3$, —$CH_2CH_2$—O—$CH_2CH_3$, —$CH_2CH_2CH_2$—O—$CH_2CH_3$, —$CH_2CH_2$—O—$CH(CH_3)$, and —$CH_2CH_2CH_2$—O—$CH(CH_3)$.

Examples of hydroxy-($C_1$ to $C_4$)-alkoxy residues are —O—$CH_2$—OH, —O—$CH_2CH_2OH$, —O—$CH_2CH_2CH_2OH$, —O—$CHCH(OH)CH_3$, and —O—$CH_2CH_2CH_2CH_2OH$.

Examples of ($C_1$ to $C_4$) acetylaminoalkoxy residues are —O—$CH_2NHC(O)CH_3$, —O—$CH_2CH_2NHC(O)CH_3$, —O—$CH_2CH_2CH_2NHC(O)CH_3$, —O—$CHCH(NHC(O)CH_3)CH_3$, and —O—$CH_2CH_2CH_2CH_2NHC(O)CH_3$.

Examples of ($C_1$ to $C_4$) carbamoylaminoalkoxy residues are —O—$CH_2CH_2$—NH—C(O)—$NH_2$, —O—$CH_2CH_2CH_2$—NH—C(O)—$NH_2$, and —O—$CH_2CH_2CH_2CH_2$—NH—C(O)—$NH_2$.

Examples of ($C_1$ to $C_4$) aminoalkyl residues are —$CH_2NH_2$, —$CH_2CH_2NH_2$, —$CH_2CH_2CH_2NH_2$, —$CHCH(NH_2)CH_3$, and —$CH_2CH_2CH_2NH_2$.

Examples of ($C_1$ to $C_4$) cyanoalkyl residues are —$CH_2CN$, —$CH_2CH_2CN$, and —$CH_2CH_2CH_2CN$.

Examples of ($C_1$ to $C_4$) hydroxyalkylamino-($C_1$ to $C_4$)-alkyl residues are —$CH_2CH_2NH$—$CH_2CH_2$—OH, —$CH_2CH_2CH_2NH$—$CH_2CH_2OH$, —$CH_2CH_2NH$—$CH_2CH_2CH_2OH$, and —$CH_2CH_2CH_2NH$—$CH_2CH_2CH_2OH$.

Examples of di[($C_1$ to $C_4$)-hydroxyalkyl]amino-($C_1$ to $C_4$)-alkyl residues are —$CH_2CH_2N(CH_2CH_2$—$OH)_2$, —$CH_2CH_2CH_2N(CH_2CH_2OH)_2$, —$CH_2CH_2N(CH_2CH_2CH_2OH)_2$, and —$CH_2CH_2CH_2N(CH_2CH_2CH_2OH)_2$.

An example of aryl groups is the phenyl group.

Examples of aryl-($C_1$ to $C_4$)-alkyl groups are the benzyl group and the 2-phenylethyl group.

In a preferred embodiment, coupler components include:

m-aminophenol and the derivatives thereof such as for example 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)phenol, N-cyclopentyl-3-aminophenol, 1,3-dihydroxy-5-(methylamino)-benzene, 3-ethylamino-4-methylphenol and 2,4-dichloro-3-aminophenol;

o-aminophenol and the derivatives thereof;

m-diaminobenzene and the derivatives thereof such as for example 2,4-diaminophenoxyethanol, 1,3-bis-(2',4'-diaminophenoxy)propane, 1-methoxy-2-amino-4-(2'-hydroxyethylamino)benzene, 1,3-bis-(2',4'-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-[(3-morpholin-4-ylphenyl)amino]ethanol, 3-amino-4-(2-methoxyethoxy)-5-methylphenylamine and 1-amino-3-bis-(2'-hydroxyethyl)-aminobenzene;

o-diaminobenzene and the derivatives thereof such as for example 3,4-diaminobenzoic acid and 2,3-diamino-1-methylbenzene;

di- or trihydroxybenzene derivatives such as for example resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene;

pyridine derivatives such as for example 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine;

naphthalene derivatives such as for example 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene;

morpholine derivatives such as for example 6-hydroxybenzomorpholine and 6-aminobenzomorpholine;

quinoxaline derivatives such as for example 6-methyl-1,2,3,4-tetrahydroquinoxaline;

pyrazole derivatives such as for example 1-phenyl-3-methylpyrazol-5-one;

indole derivatives such as for example 4-hydroxyindole, 6-hydroxyindole and 7-hydroxyindole;

pyrimidine derivatives, such as for example 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine; or methylenedioxybenzene derivatives such as for example 1-hydroxy-3,4-methylenedioxybenzene, 1-amino-3,4-methylenedioxybenzene and 1-(2'-hydroxyethyl)-amino-3,4-methylenedioxybenzene;

and the physiologically acceptable salts thereof.

Coupler components which are particularly preferred are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

In an exemplary embodiment, the agents contain the additional developer components in a quantity of from about 0.005 to about 10 wt. %, preferably of from about 0.1 to about 5 wt. %, in each case relative to the total agent.

The agents more preferably contain the additional coupler components in a quantity of from about 0.005 to about 10 wt. %, preferably of from about 0.1 to about 5 wt. %, in each case relative to the total agent.

in another exemplary embodiment, those indoles and indolines which may be used in the agents as precursors of nature-analogous dyes are those which comprise at least one hydroxy or amino group, preferably as a substituent on the six-membered ring. These groups may bear further substituents, for example in the form of an etherification or esterification of the hydroxyl group or alkylation of the amino group. In another exemplary embodiment, the dyeing agents contain at least one derivative of indole and/or indoline.

Derivatives of 5,6-dihydroxyindoline of the formula VIIIa are particularly suitable as precursors of nature-analogous hair dyes,

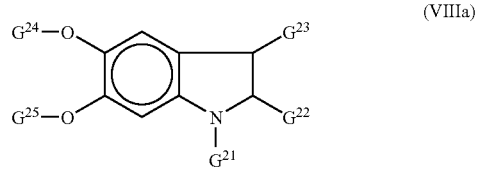

(VIIIa)

in which, mutually independently;

$G^{21}$ denotes hydrogen, a $C_1$-$C_4$ alkyl group or a $C_1$-$C_4$ hydroxyalkyl group;

$G^{22}$ denotes hydrogen or a —COOH group, the —COOH group possibly also assuming the form of a salt with a physiologically acceptable cation;

$G^{23}$ denotes hydrogen or a $C_1$-$C_4$ alkyl group;

$G^{24}$ denotes hydrogen, a $C_1$-$C_4$ alkyl group or a —CO-$G^{26}$ group, in which $G^{26}$ denotes a $C_1$-$C_4$ alkyl group; and $G^{25}$ denotes one of the groups stated under $G^{24}$, and physiologically acceptable salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis should be placed on N-methyl-5,6-dihydroxyindoline, N-ethyl-5,6-dihydroxyin-doline, N-propyl-5,6-dihydroxyindoline, N-butyl-5,6-dihydroxyindoline and in particular 5,6-dihydroxyindoline.

Derivatives of 5,6-dihydroxyindole of the formula VIIIb are furthermore outstandingly suitable as precursors of nature-analogous hair dyes,

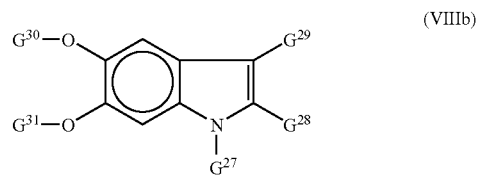

(VIIIb)

in which, mutually independently;

$G^{27}$ denotes hydrogen, a $C_1$-$C_4$ alkyl group or a $C_1$-$C_4$ hydroxyalkyl group;

$G^{28}$ denotes hydrogen or a —COOH group, the —COOH group possibly also assuming the form of a salt with a physiologically acceptable cation;

$G^{29}$ denotes hydrogen or a $C_1$-$C_4$ alkyl group;

$G^{30}$ denotes hydrogen, a $C_1$-$C_4$ alkyl group or a —CO-$G^{32}$ group, in which $G^{32}$ denotes a $C_1$-$C_4$ alkyl group; and $G^{31}$ denotes one of the groups stated under $G^{30}$;

and physiologically acceptable salts of these compounds with an organic or inorganic acid.

Particularly preferred indole derivatives are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group emphasis should be laid on N-methyl-5,6-dihydroxyindole, N-ethyl-5,6-dihydroxyindole, N-propyl-5,6-dihydroxyindole, N-butyl-5,6-dihydroxyindole, and in particular 5,6-dihydroxyindole.

In an exemplary embodiment, in the dyeing agents, the indoline and indole derivatives may be used both as free bases and in the form of the physiologically acceptable salts thereof with inorganic or organic acids, for example hydrochlorides, sulfates and hydrobromides. In one embodiment, the indole or indoline derivatives are contained therein conventionally in quantities of from about 0.05 to about 10 wt. %, preferably of from about 0.2 to about 5 wt. %

The presence of oxidizing agents, for example $H_2O_2$, may be dispensed with, in particular if the agent does not contain any oxidation dye precursors. If the agent contains air-oxidizable oxidation dye precursors or indole or indoline derivatives, it is straightforwardly possible to dispense with oxidizing agents. It may however possibly be desirable to add hydrogen peroxide or other oxidizing agents to the agents to achieve shades which are lighter than the keratin-containing fibers to be dyed. Oxidizing agents are generally used in a quantity of from about 0.01 to about 6 wt. % relative to the application solution. An oxidizing agent preferred for human hair is $H_2O_2$. Mixtures of a plurality of oxidizing agents, such as for example a combination of hydrogen peroxide and peroxodisulfates of the alkali and alkaline earth metals or of iodide ion sources, such as for example alkali metal iodides and hydrogen peroxide or the above-stated peroxodisulfates, may be used. The oxidizing agent or oxidizing agent combination may be used in the hair dyeing agent in conjunction with oxidation catalysts. Oxidation catalysts are for example metal salts, metal chelate complexes or metal oxides, which enable an easy change between two oxidation stages of the metal ions. Examples are salts, chelate complexes or oxides of iron, ruthenium, manganese and copper. Further possible oxidation catalysts take the form of enzymes. Suitable enzymes are for example peroxidases, which are capable of distinctly enhancing the action of small quantities of hydrogen peroxide. Enzymes which are furthermore suitable for use in the agents are those which, with the assistance of atmospheric oxygen, directly oxidize the oxidation dye precursors, such as laccases for example, or which produce small quantities of hydrogen peroxide in situ and so biocatalytically activate oxidation of the dye precursors. Particularly suitable catalysts for the oxidation of dye precursors are "two-electron oxidoreductases" in combination with their specific substrates, for example:

pyranose oxidase and for example D-glucose or galactose;
glucose oxidase and D-glucose;
glycerol oxidase and glycerol;
pyruvate oxidase and pyruvic acid or the salts thereof;
alcohol oxidase and alcohol (MeOH, EtOH);
lactate oxidase and lactic acid and the salts thereof;
tyrosinase oxidase and tyrosine;
uricase and uric acid or the salts thereof;
choline oxidase and choline; and
amino acid oxidase and amino acids.

In another exemplary embodiment, for further modification of the color shades, the dyeing agents contemplated herein also contain conventional direct dyes, such as nitrophenylenediamines, nitroaminophenols, azo dyes, anthraquinones or indophenols. Preferred direct dyes are the compounds known by the international names or trade names HC Yellow 2HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52 as well as 1,4-diamino-2-nitrobenzene, 2-amino-4-nitrophenol, 1,4-bis-(β-hydroxyethyl)-amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-1-hydroxy-4-nitrobenzene.

In an exemplary embodiment, the agents may furthermore contain a cationic direct dye. Particular preference is here given to:
(a) cationic triphenylmethane dyes, such as for example Basic Blue 7, Basic Blue 26, Basic Violet 2 and Basic Violet 14;
(b) aromatic systems substituted with a quaternary nitrogen group, such as for example Basic Yellow 57, Basic Red 76, Basic Blue 99, Basic Brown 16 and Basic Brown 17; and
(c) direct dyes containing at least one heterocycle which comprises at least one quaternary nitrogen atom, as are for example mentioned in claims 6 to 11 of EP-A2-998 908, to which explicit reference is made here.

Preferred cationic direct dyes of group (c) are in particular the following compounds.

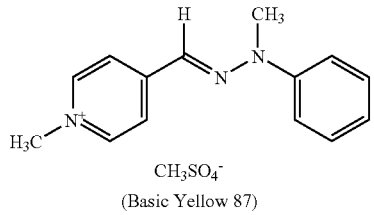
(Basic Yellow 87) (DZ1)

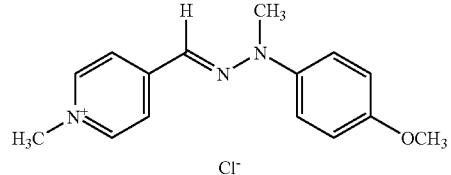
(DZ2)

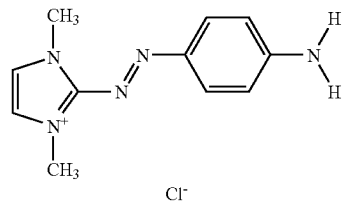
(Basic Orange 31) (DZ3)

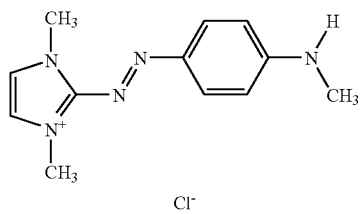
(DZ4)

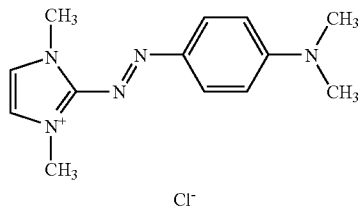
(Basic Red 51) (DZ5)

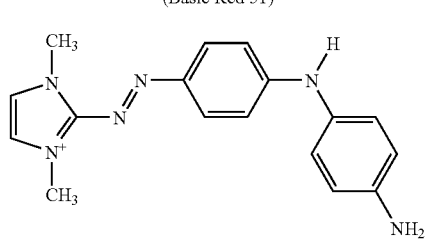
(DZ6)

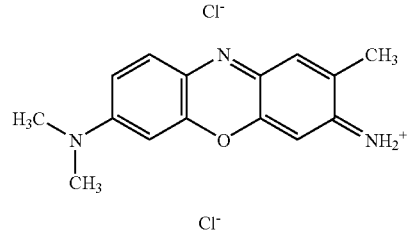
(DZ7)

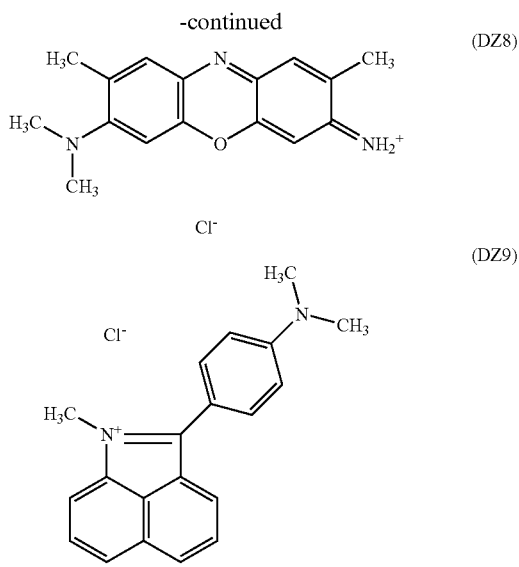

The compounds of the formulae (DZ1), (DZ3) and (DZ5) are very particularly preferred cationic direct dyes of group (c). The cationic direct dyes distributed under the trademark Arianor® are direct dyes which are particularly preferred.

In one exemplary embodiment, agents contain the direct dyes in a quantity of from about 0.01 to about 20 wt. %, relative to the entire dyeing agent.

Furthermore, the preparations may also contain naturally occurring dyes, such as are contained for example in henna red, henna neutral, henna black, chamomile flowers, sandalwood, black tea, alder buckthorn bark, sage, logwood, madder root, catechu, lotus tree and alkanet root.

It is not necessary for the optionally present direct dyes in each case to be uniform compounds. Instead, as a result of the production processes for the individual dyes, the dyeing agents contemplated herein may contain subordinate quantities of still further components, provided that these do not have a disadvantageous effect on the dyeing result or must be excluded for other, for example toxicological, reasons.

To achieve further, more intense coloration, the agents may additionally contain color enhancers. The color enhancers are preferably selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, the derivatives thereof and the physiologically acceptable salts thereof.

The above-stated color enhancers may be used in a quantity of in each case from about 0.03 to about 10 wt. %, preferably from about 0.5 to about 5 wt. %, in each case relative to 100 g of the ready-to-use dyeing agent.

In an exemplary embodiment, the agents may have a pH value of about pH 4 to about 12, preferably of about pH 5 to about 10.

The dyeing agents contemplated herein produce more intense dyeing results even at physiologically acceptable temperatures of below 45° C. They are therefore particularly suitable for dyeing human hair. For application to human hair, the dyeing agents are conventionally incorporated into a hydrous cosmetic carrier. Suitable hydrous cosmetic carriers are for example creams, emulsions, gels or also surfactant-containing foaming solutions, such as for example shampoos or other preparations which are suitable for use on keratin-containing fibers. If necessary it is also possible to incorporate the dyeing agent into anhydrous carriers.

The cosmetic carrier may take the form in particular of an otherwise conventional carrier of agents for dyeing human hair. The dyeing agents may, apart from the components described above, be composed in the same way as known dyeing agents or contain the ingredients conventional therefor. Examples of further suitable ingredients preferred are stated hereinafter.

In an exemplary embodiment, the agents contain the compounds of the formula (I) and the component B compounds in a suitable aqueous, alcoholic or aqueous-alcoholic carrier. Carriers suitable for the purpose of hair dyeing are for example creams, emulsions, gels or also surfactant-containing foaming solutions, such as for example shampoos, foam aerosols or other preparations which are suitable for use on the hair. It is also feasible, however, to incorporate the dye precursors into a pulverulent or also tablet-shaped formulation.

As used herein, aqueous-alcoholic solutions should be taken to be aqueous solutions containing about 3 to about 70 wt. % of a $C_1$-$C_4$ alcohol, in particular ethanol or isopropanol. The preparations may additionally contain further organic solvents, such as for example methoxybutanol, benzyl alcohol, diethylene glycol monoethyl ether or 1,2-propylene glycol. Any water-soluble organic solvents are here preferred.

In various exemplary embodiments, the dyeing agents contain at least one surfactant, in principle not only anionic but also zwitterionic, ampholytic, nonionic and cationic surfactants being suitable. In many cases, however, it has proven advantageous to select the surfactants from among anionic, zwitterionic or nonionic surfactants.

Anionic surfactants which are suitable in preparations of the dyeing agents are any anionic surface-active substances suitable for use on the human body. These are characterized by an anionic water-solubilizing group such as for example a carboxylate, sulfate, sulfonate or phosphate group and a lipophilic alkyl group having some 10 to 22 C atoms. The molecule may additionally contain glycol or polyglycol ether groups, ester, ether and amide groups and hydroxyl groups. Examples of suitable anionic surfactants are, in each case in the form of the sodium, potassium and ammonium and the mono-, di- and trialkanolammonium salts having 2 or 3 C atoms in the alkanol group:

linear fatty acids having 10 to 22 C atoms (soaps);
ether carboxylic acids of the formula R—O—($CH_2$—$CH_2O)_x$—$CH_2$—COOH, in which R is a linear alkyl group having 10 to 22 C atoms and x=0 or 1 to 16;
acyl sarcosides having 10 to 18 C atoms in the acyl group;
acyl taurides having 10 to 18 C atoms in the acyl group;
acyl isethionates having 10 to 18 C atoms in the acyl group;
sulfosuccinic acid mono- and dialkyl esters having 8 to 18 C atoms in the alkyl group and sulfosuccinic acid monoalkyl polyoxyethyl esters having 8 to 18 C atoms in the alkyl group and 1 to 6 oxyethyl groups;
linear alkanesulfonates having 12 to 18 C atoms;
linear alpha-olefin sulfonates having 12 to 18 C atoms;
alpha-sulfofatty acid methyl esters of fatty acids having 12 to 18 C atoms;
alkyl sulfates and alkyl polyglycol ether sulfates of the formula R—O($CH_2$—$CH_2O)_x$—$SO_3H$, in which R is a preferably linear alkyl group having 10 to 18 C atoms and x=0 or 1 to 12;
mixtures of surface-active hydroxysulfonates according to German patent DE-A-37 25 030;

sulfated hydroxyalkyl polyethylene and/or hydroxyalkylene propylene glycol ethers according to German patent DE-A-37 23 354;

sulfonates of unsaturated fatty acids having 12 to 24 C atoms and 1 to 6 double bonds according to German patent DE-A-39 26 344; and esters of tartaric acid and citric acid with alcohols, which are addition products of approx. 2-15 molecules of ethylene oxide and/or propylene oxide onto fatty alcohols having 8 to 22 C atoms.

Preferred anionic surfactants are alkyl sulfates, alkyl polyglycol ether sulfates and ether carboxylic acids having 10 to 18 C atoms in the alkyl group and up to 12 glycol ether groups per molecule and in particular salts of saturated and in particular unsaturated $C_8$-$C_{22}$ carboxylic acids, such as oleic acid, stearic acid, isostearic acid and palmitic acid.

Those surface-active compounds which bear at least one quaternary ammonium group and at least one —COO$^{(-)}$ or —SO$_3^{(-)}$ group on each molecule are designated as zwitterionic surfactants. Particularly suitable zwitterionic surfactants are "betaines" such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 C atoms in the alkyl or acyl group and cocoacylaminoethylhydroxyethylcarboxymethyl glycinate. One preferred zwitterionic surfactant is the fatty acid amide derivative known by the CTFA name Cocamidopropyl Betaine.

Ampholytic surfactants are taken to mean those surface-active compounds which, in addition to a $C_{8-18}$ alkyl or acyl group, contain at least one free amino group and at least one —COON or —SO$_3$H group per molecule and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case approximately 8 to 18 C atoms in the alkyl group. Particularly preferred ampholytic surfactants are N-cocoalkyl aminopropionate, cocoacylaminoethyl aminopropionate and $C_{12-18}$ acyl sarcosine.

Nonionic surfactants contain a hydrophilic group for example a polyol group, a polyalkylene glycol ether group or a combination of a polyol group and polyglycol ether group. Such compounds are for example:

addition products of 2 to 30 mol of ethylene oxide and/or 0 to 5 mol of propylene oxide onto linear fatty alcohols having 8 to 22 C atoms, onto fatty acids having 12 to 22 C atoms, and onto alkylphenols having 8 to 15 C atoms in the alkyl group;

$C_{12-22}$ fatty acid mono- and diesters of addition products of 1 to 30 mol of ethylene oxide onto glycerol;

$C_{8-22}$ alkyl mono- and oligoglycosides and the ethoxylated analogues thereof, addition products of 5 to 60 mol of ethylene oxide onto castor oil and hardened castor oil;

addition products of ethylene oxide onto sorbitan fatty acid esters; and addition products of ethylene oxide onto fatty acid alkanolamides.

Examples of cationic surfactants usable in the hair treatment agents contemplated herein are in particular quaternary ammonium compounds. Preference is given to ammonium halides such as alkyltrimethylammonium chlorides, dialkyldimethylammonium chlorides and trialkylmethylammonium chlorides, for example cetyltrimethylammonium chloride, stearyltrimethylammonium chloride, distearyldimethylammonium chloride, lauryldimethylammonium chloride, lauryldimethylbenzylammonium chloride and tricetylmethylammonium chloride. Quaternized protein hydrolysates are further cationic surfactants which are suitable for use in the hair treatment agents.

Cationic silicone oils are likewise suitable, such as for example the commercially obtainable products Q2-7224 (manufacturer: Dow Corning; a stabilized trimethylsilylamodimethicone), Dow Corning 929 Emulsion (containing a hydroxylamine-modified silicone which is also designated an amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxane, Quaternium-80).

Alkylamidoamines, in particular fatty acid amidoamines such as stearylamidopropyldimethylamine obtainable under the name Tego Amide®S 18 are distinguished by good biodegradability in addition to having a good conditioning action.

Quaternary ester compounds, known as "ester quats", such as the methylhydroxyalkyldialkoyloxyalkylammonium methosulfates distributed under the trade mark Stepantex® are likewise very highly biodegradable.

One example of a quaternary sugar derivative usable as a cationic surfactant is the commercial product Glucquat®100, according to CTFA nomenclature a "Lauryl Methyl Gluceth-10 Hydroxypropyl Dimonium Chloride".

The compounds with alkyl groups used as surfactants may in each case comprise uniform substances. It is, however, generally preferred to start from native plant or animal raw materials when producing these substances, such that mixtures of substances having a differing alkyl chain length depending on the particular raw material are obtained.

The surfactants which are addition products of ethylene and/or propylene oxide onto fatty alcohols or derivatives of these addition products may be used both as products with a "normal" homologue distribution and as products with a narrow homologue distribution. A "normal" homologue distribution is here taken to mean mixtures of homologues which are obtained on reacting fatty alcohol and alkylene oxide using alkali metals, alkali metal hydroxides or alkali metal alkoxides as catalysts. Narrow homologue distributions, in contrast, are obtained if hydrotalcite, alkaline earth metal salts of ether carboxylic acids, alkaline earth metal oxides, hydroxides or alkoxides are for example used as catalysts. It may be preferred to use products with a narrow homologue distribution.

Further active ingredients and auxiliary substances and additives are for example:

nonionic polymers such as for example vinylpyrrolidone/vinyl acrylate copolymers, polyvinylpyrrolidone and vinylpyrrolidone/vinyl acetate copolymers and polysiloxanes;

cationic polymers such as quaternized cellulose ethers, polysiloxanes with quaternary groups, dimethyldiallylammonium chloride polymers, acrylamide/dimethyldiallylammonium chloride copolymers, dimethylaminoethyl methacrylate/vinylpyrrolidone copolymers quaternized with diethyl sulfate, vinylpyrrolidone/imidazolinium methochloride copolymers and quaternized polyvinyl alcohol;

zwitterionic and amphoteric polymers such as for example acrylamidopropyltrimethylammonium chloride/acrylate copolymers, and octylacrylamide/methyl methacrylate/tert.-butylaminoethyl methacrylate/2-hydroxypropyl methacrylate copolymers;

anionic polymers such as for example polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.-butylacrylamide terpolymers;

thickeners such as agar-agar, guar gum, alginates, xanthan gum, gum arabic, karaya gum, locust bean flour, linseed gums, dextrans, cellulose derivatives, for example methylcellulose, hydroxyalkylcellulose and carboxymethylcellulose, starch fractions and derivatives such as amylose, amylopectin and dextrins, clays such as for example bentonite or completely synthetic hydrocolloids such as for example polyvinyl alcohol;

structuring agents such as glucose and maleic acid;

hair-conditioning compounds such as phospholipids, for example soy lecithin, egg lecithin and cephalins, as well as silicone oils;

protein hydrolysates, in particular elastin, collagen, keratin, milk protein, soy protein and wheat protein hydrolysates, the condensation products thereof with fatty acids and quaternized protein hydrolysates;

perfume oils, dimethyl isosorbide and cyclodextrins;

solubilizing agents such as ethanol, isopropanol, ethylene glycol, propylene glycol, glycerol and diethylene glycol;

antidandruff active ingredients such as piroctone olamine and zinc omadine;

further substances for adjusting the pH value, such as ammonia, monoethanolamine, basic amino acids and citric acid;

active ingredients such as panthenol, pantothenic acid, allantoin, pyrrolidonecarboxylic acids and the salts thereof, plant extracts and vitamins;

cholesterol;

light stabilizers;

consistency providers, such as sugar esters, polyol esters or polyol alkyl ethers;

fats and waxes such as spermaceti, beeswax, montan wax, paraffins, fatty alcohols and fatty acid esters;

fatty acid alkanolamides;

complexing agents such as EDTA, NTA and phosphonic acids;

swelling and penetrating substances such as glycerol, propylene glycol monoethyl ether, carbonates, hydrogencarbonates, guanidines, ureas and primary, secondary and tertiary phosphates, imidazoles, tannins, pyrrole;

opacifiers such as latex;

pearlescent agents such as ethylene glycol mono- and distearate;

propellants such as propane/butane mixtures, $N_2O$, dimethyl ether, $CO_2$ and air; and antioxidants.

In an exemplary embodiment, the constituents of the hydrous carrier are used to produce the dyeing agents in quantities conventional for this purpose; for example, emulsifiers are used in concentrations of from about 0.5 to about 30 wt. % and thickeners in concentrations of from about 0.1 to about 25 wt. % of the total dyeing agent.

It may be advantageous for the dyeing result to add ammonium or metal salts to the dyeing agents. Suitable metal salts are for example formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminum, manganese, iron, cobalt, copper or zinc, with sodium acetate, lithium bromide, calcium bromide, calcium gluconate, zinc chloride, zinc sulfate, magnesium chloride, magnesium sulfate, ammonium carbonate, chloride and acetate being preferred. These salts are preferably contained in a quantity of from about 0.03 to about 10 wt. %, preferably of from about 0.5 to about 5 wt. %, relative to 100 g of the total, ready-to-use dyeing agent.

In an exemplary embodiment, the pH value of the ready-to-use dyeing agents is between about 2 and about 11, preferably between about 5 and about 10.

Also contemplated herein is the use of at least one compound according to the formula I,

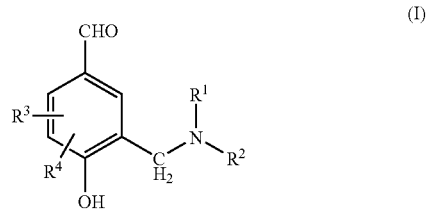

in which $R^1$, $R^2$, $R^3$ and $R^4$ are defined above, together with at least one CH-acidic compound as component B as the dyeing component in hair dyeing agents.

In a preferred embodiment, those compounds which are used according to the formula I as a dyeing component in hair dyeing agents are those selected from the preferred and particularly preferred representatives mentioned above.

It may additionally be preferable to use at least one reaction product RP from a compound according to the formula I and a representative of component B as the dyeing components in hair dyeing agents.

In one exemplary embodiment, a method of dyeing keratin-containing fibers, in particular human hair, comprises applying to keratin-containing fibers a dyeing agent, containing in a cosmetic carrier:

as component A at least one compound according to the formula I,

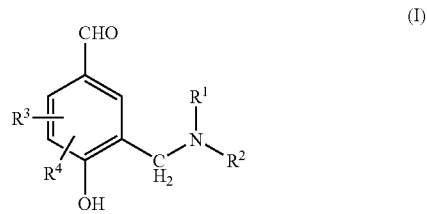

in which $R^1$, $R^2$, $R^3$ and $R^4$ are defined above, together with at least one CH-acidic compound as component B, leaving the dyeing agent on the fibers for a period of time, for example about 15 to about 30 minutes, and then rinsing out the dyeing agent or washing out the dyeing agent with a shampoo. While the agent is acting on the fiber it may be advantageous to assist the dyeing process by supplying heat. Heat may be supplied by an external heat source, such as for example hot air from a hot air blower, and also, in particular when dyeing the hair of a living test subject, by the body temperature of the test subject. In the case of the latter possibility, the part to be dyed is covered with a cap.

In this case, the compounds according to the formula I and the component B compounds, in particular the above-mentioned preferred and particularly preferred representatives thereof, may be applied as color-imparting components either simultaneously to the hair or alternatively one after the other, i.e. in a multistage method, it being immaterial which of the components is applied first. The optionally contained ammonium or metal salts may then be added to the compounds of the formula I or to the component B compounds. A period of up to 30 minutes may be left between application of the individual components. Pretreatment of the fibers with the salt solution is possible.

In one exemplary embodiment, prior to application of the dyeing agent it may be desirable to subject the keratin-containing fibers to a pretreatment. The pretreatment step necessary therefor and the application of the agent do not have to take place chronologically in immediate succession, but rather a period of at most two weeks may be left between the pretreatment step and application of the agent according to the invention. A plurality of pretreatment methods are suitable for this purpose, for example:

subjecting the fibers to bleaching prior to application of the agent; or subjecting the fibers to oxidative dyeing prior to application of the agent.

For the purposes of pretreatment by bleaching the fibers, the keratin-containing fibers are treated with a bleaching preparation. The bleaching preparation preferably contains in addition to an oxidizing agent, such as conventionally hydrogen peroxide, at least one inorganic per-salt active as an oxidation and bleach booster, such as for example a peroxodisulfate of sodium, potassium or ammonium. As a result of pretreatment by bleaching, the dyeing results obtained using the above-described method obtain particular brightness and color depth.

For the purposes of pretreatment by oxidative dyeing, an agent containing above-stated oxidation dye precursors as developer and optionally coupler components and optionally above-stated derivatives of indole or indoline is applied to the fibers and left on the keratin fibers/hair for about 5 to about 45 minutes after an exposure time optionally with the addition of above-stated suitable oxidizing agents. Then the hair is rinsed. Through subsequent application of a dyeing agent contemplated herein, a new color shade may be imparted to the existing oxidation dyeing result. If the color shade of the dyeing agent is selected to be the same as the oxidative dyeing color shade, the color of the existing oxidation dyeing results may be freshened up by the method described above. It has been found that color freshening or shading using the method described above is superior in color brightness and color depth to color freshening or shading solely with conventional direct dyes.

If, in addition to the compounds according to the formula I and the component B compounds, the hair dyeing agent additionally contains as oxidizing agents hydrogen peroxide or an oxidizing agent mixture containing hydrogen peroxide, the pH value of the hydrogen peroxide-containing hair dyeing agent is preferably in a pH range of from about pH 7 to about pH 11, more preferably about pH 8 to about pH 10. The oxidizing agent may be mixed with the hair dyeing agent immediately prior to use and the mixture applied to the hair. If the compounds of the formula I and component B are applied onto the hair in a two-stage method, the oxidizing agent should be applied in one of the two method steps together with the corresponding color-imparting component. For this purpose it may be preferable for the oxidizing agents to be formulated with one of the color-imparting components in a container.

The compounds according to the formula of FIG. 1 and the component B compounds may either be stored in separate containers or together in one container, either in a liquid to pasty preparation (aqueous or anhydrous) or as a solid, for example as a dry powder. If the components are stored together in a liquid preparation, in order to reduce the likelihood of the components reacting, the preparation should be largely anhydrous and a have an acidic pH value. If the components are stored together, it is preferable for them to be formulated as a solid, in particular in the form of a preferred multilayer molding, for example as a tablet. In the case of the multilayer molding, component A is incorporated into one layer and component B into another layer, a further layer preferably being situated between these layers as a separation layer. The separation layer is free of component A and B compounds. In the case of separate storage, the reactive components are intimately mixed together only immediately prior to application. In the case of dry storage, a defined quantity of hot (30° C. to 80° C.) water is conventionally added prior to application and a homogeneous mixture produced.

In another exemplary embodiment, a method for shading oxidation dyed keratin-containing fibers, in particular human hair, comprises using:

at least one compound according to the formula I,

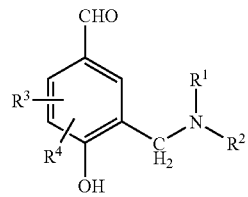

(I)

in which $R^1$, $R^2$, $R^3$ and $R^4$ are defined above with respect to formula I, together with at least one CH-acidic compound as component B.

In the case of use, it is immaterial whether shading takes place at the same time as the oxidative dyeing or the oxidative dyeing takes place before shading.

In a further exemplary embodiment, a method for freshening up the color of keratin-containing fibers dyed with oxidative dyeing agents comprises using:

at least one compound according to the formula I, in which $R^1$, $R^2$, $R^3$ and $R^4$ are defined above, together with at least one CH-acidic compound as component B.

The dyeing results for keratin-containing fibers are known to be exposed to environmental influences, such as for example light, friction or washing, and may lose brightness and color depth as a consequence. In the worst case, the color may undergo a shift in shade. Such aged dyeing results for keratin-containing fibers may, if the user wishes, be restored by color freshening roughly to the colored state as prevailed immediately after the original dyeing procedure. As contemplated herein, such color freshening may be achieved by using a combination of at least one compound of the formula I and at least one component B compound.

EXAMPLES

The following examples are provided for illustration purposes only and are not meant to limit the various embodiments of the present invention in any way.

Synthesis Examples

Synthesis Example 1

Preparation of 3-[(dimethylamino)methyl]-4-hydroxy-5-methoxybenzaldehyde (A1)

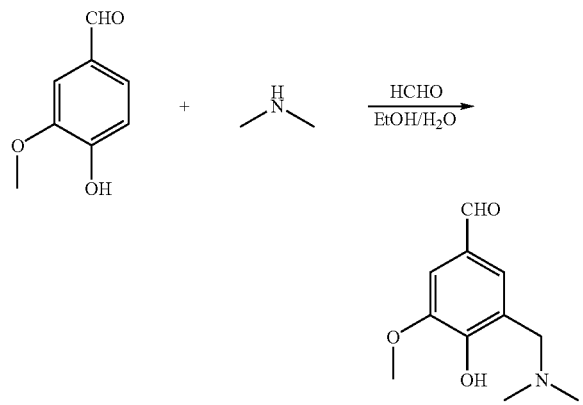

18.0 g (0.15 mol) of a 40% aqueous dimethylamine solution were added to 12.0 g (0.15 mol) of a 37% aqueous formaldehyde solution in 90 ml of ethanol. Then 15.2 g (0.10 mol) of 4-hydroxy-3-methoxybenzaldehyde (vanillin) were added. The reaction mixture was refluxed for 30 minutes and stirred for a further 24 hours at room temperature. Then the reaction mixture was left to stand overnight in the refrigerator at 0 to 5° C. The precipitated solid was filtered out, washed with ice-cold acetone and dried. The result was a white powder.

Yield: 14.6 g (69.9%)

$^1$H-NMR (400 MHz, DMSO-$d_6$): δ parts per million (ppm)=2.30 (s, 6H); 3.74 (s, 2H); 3.82 (s, 3H); 7.29 (s, 1H); 7.30 (s, 1H); 9.71 (s, 1H)

$^{13}$C-NMR (400 MHz, DMSO-$d_6$): δ [ppm]=43.8; 55.5; 59.7; 109.9; 122.3; 125.7; 126.9; 148.4; 154.6; 191.1

Synthesis Example 2

Preparation of 4-hydroxy-3-methoxy-5-(pyrrolidin-1-ylmethyl)benzaldehyde (A2)

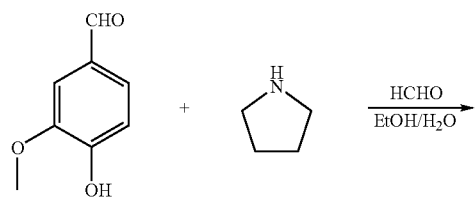

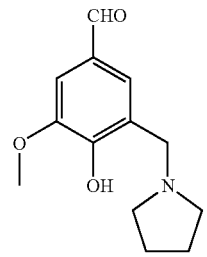

21.3 g (0.30 mol) of pyrrolidine were added to 24.0 g (0.30 mol) of a 37% aqueous formaldehyde solution in 180 ml of ethanol. Then 30.4 g (0.20 mol) of 4-hydroxy-3-methoxybenzaldehyde (vanillin) were added. The mixture was refluxed for three hours. A solid began to precipitate out as early as during cooling, which was filtered out after complete cooling of the reaction batch and dried.

Yield: 22.0 g (46.8%)

$^1$H-NMR (400 MHz, DMSO-$d_6$): δ [ppm]=1.80 (m, 4H); 2.68 (m, 4H); 3.86 (s, 3H); 3.91 (s, 2H); 7.29 (s, 1H); 7.33 (s, 1H); 9.71 (s, 1H)

$^{13}$C-NMR (400 MHz, DMSO-$d_6$): δ [ppm]=23.4; 53.9; 55.4; 56.0; 109.8; 122.5; 125.8; 126.4; 147.4; 155.1; 190.7

Synthesis Example 3

Preparation of 4-hydroxy-3-methoxy-5-(piperidin-1-ylmethyl)benzaldehyde (A3)

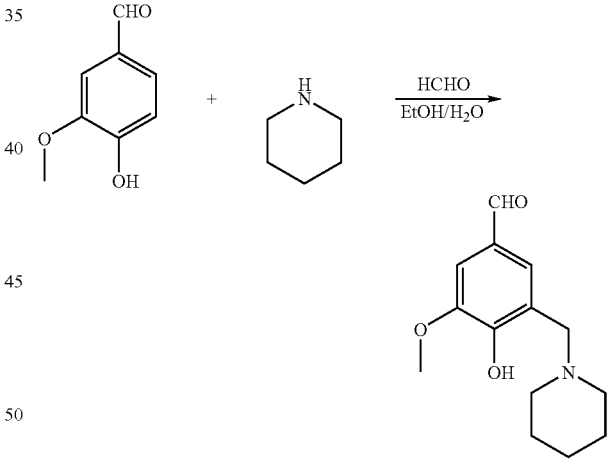

25.5 g (0.30 mol) of piperidine were added to 24.0 g (0.30 mol) of a 37% aqueous formaldehyde solution in 180 ml of ethanol. Then 30.4 g (0.20 mol) of 4-hydroxy-3-methoxybenzaldehyde (vanillin) were added. The reaction mixture was refluxed for one hour. A solid began to precipitate out as early as during cooling, which was filtered out after complete cooling of the reaction batch and dried.

Yield: 38.0 g (76.3%)

$^1$H-NMR (400 MHz, DMSO-$d_6$): δ [ppm]=1.41 (m, 2H); 1.51 (m, 4H); 2.5 (m, 4H); 3.77 (s, 2H); 3.85 (s, 3H); 7.32 (s, 2H); 9.71 (s, 1H)

$^{13}$C-NMR (400 MHz, DMSO-$d_6$): δ [ppm]=23.8; 25.1; 53.1; 55.8; 59.0; 109.8; 122.3; 125.4; 126.2; 147.8; 154.5; 190.9

Synthesis Example 4

Preparation of 4-hydroxy-3-methoxy-5-(morpholin-4-ylmethyl)benzaldehyde (A4)

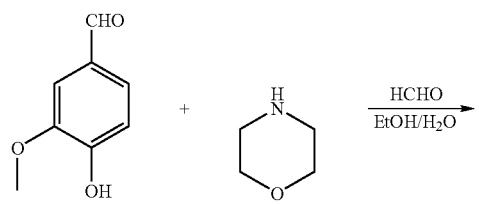

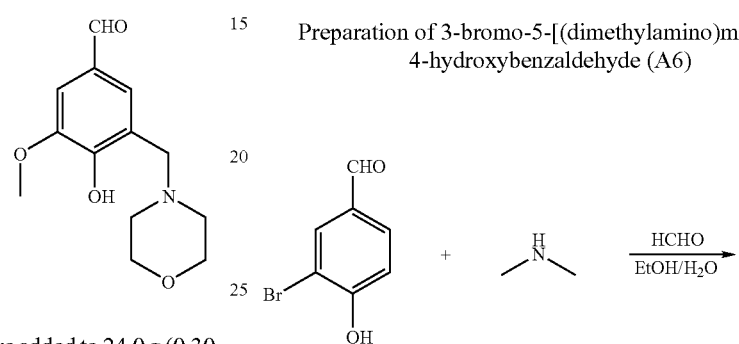

26.1 g (0.30 mol) of morpholine were added to 24.0 g (0.30 mol) of a 37% aqueous formaldehyde solution in 180 ml of ethanol. Then 30.4 g (0.20 mol) of 4-hydroxy-3-methoxybenzaldehyde (vanillin) were added. The reaction mixture was refluxed for one hour. After cooling the majority of the solvent was removed in a rotary evaporator. 250 ml of distilled water were added to the residue. After a certain time, a solid began to precipitate out, which was filtered out and dried.

Yield: 24.0 g (47.8%)

$^1$H-NMR (400 MHz, DMSO-$d_6$): δ [ppm]=2.45 (m, 4H); 3.62 (m, 4H); 3.70 (s, 2H); 3.87 (s, 3H); 7.37 (s, 1H); 7.42 (s, 1H); 9.76 (s, 1H)

$^{13}$C-NMR (400 MHz, DMSO-$d_6$): δ [ppm]=52.4; 55.9; 58.1; 66.2; 109.4; 122.9; 126.1; 128.2; 148.4; 153.0; 190.6

Synthesis Example 5

Preparation of 3-chloro-5-[(dimethylamino)methyl]-4-hydroxybenzaldehyde (A5)

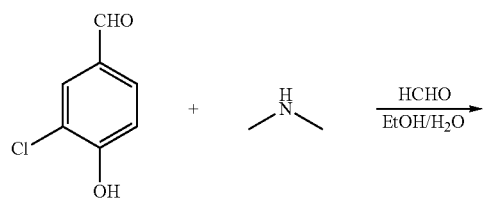

11.5 g (0.96 mol) of a 40% aqueous dimethylamine solution were added to 7.7 g (0.96 mol) of a 37% aqueous formaldehyde solution in 60 ml of ethanol. Then 10.0 g (0.64 mol) of 3-chloro-4-hydroxybenzaldehyde were added thereto. The reaction mixture was refluxed for 30 minutes and then stirred for 24 hours at room temperature. The precipitated white solid was filtered out and dried.

Yield: 6.5 g (47.8%)

$^1$H-NMR (400 MHz, $D_2O$): δ [ppm]=2.85 (s, 6H); 4.17 (s, 2H); 7.53 (s, 1H); 7.72 (s, 1H); 9.30 (s, 1H)

$^{13}$C-NMR (400 MHz, $D_2O$): δ [ppm]=44.9; 62.4; 122.3; 124.3; 127.9; 135.2 (br.); 136.5 (br.); 174.1; 194.5

Synthesis Example 6

Preparation of 3-bromo-5-[(dimethylamino)methyl]-4-hydroxybenzaldehyde (A6)

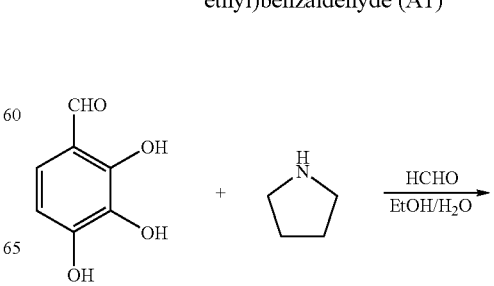

22.8 g (0.19 mol) of a 40% aqueous dimethylamine solution were added to 15.2 g (0.19 mol) of a 37% aqueous formaldehyde solution in 110 ml of ethanol. Then 25.0 g (0.12 mol) of 3-bromo-4-hydroxybenzaldehyde were added thereto. The reaction mixture was refluxed for 30 minutes and then stirred for 24 hours at room temperature. The batch was stored overnight at 0 to 5° C. in the refrigerator. The precipitated white solid was filtered out and dried.

Yield: 7.5 g (23.4%)

$^1$H-NMR (400 MHz, $D_2O$): δ [ppm]=2.87 (s, 6H); 4.20 (s, 2H); 7.54 (s, 1H); 7.90 (s, 1H); 9.29 (s, 1H)

$^{13}$C-NMR (400 MHz, $D_2O$): δ [ppm]=45.0; 63.1; 118.6; 122.4; 125.0; 136.9 (br.); 139.7 (br.); 174.8; 195.0

Synthesis Example 7

Preparation of 2,3,4-trihydroxy-5-(pyrrolidin-1-ylmethyl)benzaldehyde (A1)

-continued

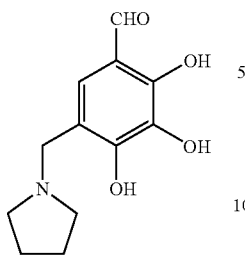

17.1 g (0.24 mol) of pyrrolidine were added to 19.2 g (0.24 mol) of a 37% aqueous formaldehyde solution in 140 ml of ethanol. Then 25.0 g (0.16 mol) of 2,3,4-trihydroxybenzaldehyde were added thereto. The reaction mixture was refluxed for one hour, developing a dark brown color. After cooling, a beige-brown solid precipitated out, which was filtered out and dried.

Yield: 15.5 g (40.3%)

$^1$H-NMR (400 MHz, DMSO-d$_6$): δ [ppm]=1.84 (m, 4H); 2.91 (m, 4H); 3.93 (s, 2H); 6.92 (s, 1H); 9.50 (s, 1H)

$^{13}$C-NMR (400 MHz, DMSO-d$_6$): δ [ppm]=22.5; 52.3; 55.4; 111.2; 114.3; 125.4; 132.8; 148.9; 162.7; 190.9

Synthesis Example 8

Preparation of 2,3,4-trihydroxy-5-(piperidin-1-ylmethyl)benzaldehyde (A1)

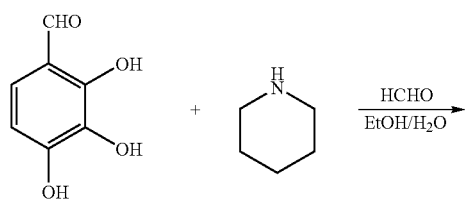

20.4 g (0.24 mol) of piperidine were added to 19.2 g (0.24 mol) of a 37% aqueous formaldehyde solution in 140 ml of ethanol. Then 25.0 g (0.16 mol) of 2,3,4-trihydroxybenzaldehyde were added thereto. The reaction mixture was refluxed for one hour, developing a dark brown color. After cooling, a beige-brown solid precipitated out, which was filtered out and dried.

Yield: 26.3 g (64.6%)

$^1$H-NMR (400 MHz, DMSO-d$_6$): δ [ppm]=1.60-1.90 (m, 6H); 2.93 (m, 2H); 3.48 (m, 2H); 4.14 (s, 2H); 7.12 (s, 1H); 9.36 (s, 1H)

$^{13}$C-NMR (400 MHz, DMSO-d$_6$): δ [ppm]=24.8; 26.5; 55.0; 60.2; 114.1; 115.0; 134.2; 135.9; 152.3; 168.2; 196.5

Synthesis Example 9

Preparation of 2,3,4-trihydroxy-5-(morpholin-4-ylmethyl)benzaldehyde (A1)

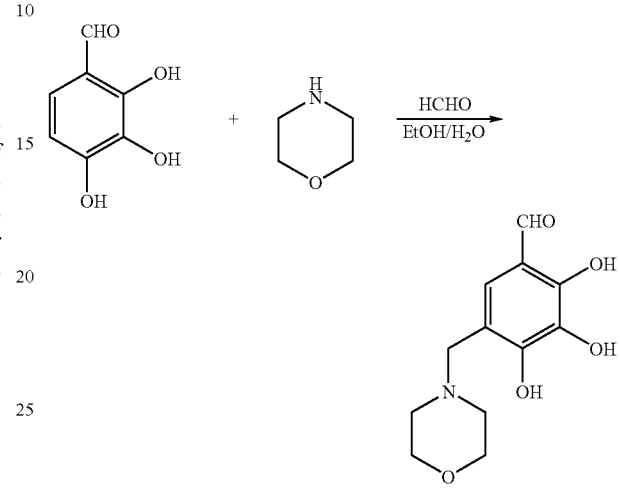

20.9 g (0.24 mol) of morpholine were added to 19.2 g (0.24 mol) of a 37% aqueous formaldehyde solution in 140 ml of ethanol. Then 25.0 g (0.16 mol) of 2,3,4-trihydroxybenzaldehyde were added thereto. The reaction mixture was refluxed for one hour, developing a dark brown color. After cooling, a beige-brown solid precipitated out, which was filtered out and dried.

Yield: 29.2 g (71.0%)

$^1$H-NMR (400 MHz, D$_2$O): δ [ppm]=3.19 (m, 4H); 3.91 (m, 4H); 4.09 (s, 2H); 7.00 (s, 1H); 9.28 (s, 1H)

$^{13}$C-NMR (400 MHz, DMSO-d$_6$): δ [ppm]=54.4; 60.2; 67.1; 114.2; 114.9; 133.9; 135.8; 152.9; 168.1; 196.2

Dyeing Examples

Production of a Dyeing Agent

| Aqueous gel formulation for component A | Gel 1 |
|---|---|
| Compound of the formula 1 (component A) | 10 mmol |
| Natrosol HR 250 | 2 g |
| NaOH (50% aqueous solution) | opt. a few drops |
| Water, deionized | ad 100 g |

| Aqueous gel formulation for component B | Gel 2 |
|---|---|
| CH-acidic compound (component B) | 10 mmol |
| Natrosol HR 250 | 2 g |
| Water, deionized | ad 100 g |

The compound (component A) was dissolved or suspended in a little water. To increase solubility, a few drops of 50% sodium hydroxide solution were added for alkalization if required. Water was then added to make up to 98 g and stirring was carried out until the aldehyde was completely dissolved (in part with mild heating to approx. 40° C.). Then Natrosol was added thereto with stirring and the swelling process was awaited.

The CH-acidic compound (component B) was initially dissolved with stirring in a little water, then made up to 98 g with water. The Natrosol was added with stirring and the swelling process awaited.

The two aqueous gel formulations (gel 1 and gel 2) were mixed together in the ratio 1:1, then the pH value was adjusted with ammonia or tartaric acid.

This resultant ready-to-use hair dyeing agent was applied to a strand of 90%-greyed, unpretreated human hair (liquor ratio of gel mixture to hair=2:1) and uniformly distributed using an applicator. After an exposure time of 30 minutes at 32° C. the strand was rinsed with lukewarm water and then dried in a hot stream of air. The dyeing results were assessed visually under a daylight lamp. The results are shown in Table 1.

TABLE 1

| Component A | Component B | pH value | Dyeing result |
| --- | --- | --- | --- |
| A1 | B1 | 9 | intense purple +++ |
| A1 | B2 | 9 | bright purple +++ |
| A1 | B3 | 9 | purple +++ |
| A1 | B4 | 9 | orange ++ |
| A2 | B1 | 9 | dark magenta +++ |
| A2 | B2 | 9 | bright reddish purple +++ |
| A2 | B3 | 9 | dark magenta +++ |
| A2 | B4 | 9 | yellow-orange +++ |
| A3 | B1 | 9 | ruby +++ |
| A3 | B2 | 9 | bright purplish red +++ |
| A3 | B3 | 9 | ruby +++ |
| A3 | B4 | 9 | orange +++ |
| A4 | B1 | 9 | port-wine red +++ |
| A4 | B2 | 9 | bright purplish red +++ |
| A4 | B3 | 9 | dark red +++ |
| A4 | B4 | 9 | orange +++ |
| A5 | B1 | 9 | intense purplish red +++ |
| A5 | B2 | 9 | ruby +++ |
| A5 | B3 | 9 | ruby +++ |
| A5 | B4 | 9 | orange +++ |
| A6 | B1 | 9 | intense purplish red +++ |
| A6 | B2 | 9 | purplish red +++ |
| A6 | B3 | 9 | ruby +++ |
| A6 | B4 | 9 | orange +++ |
| A7 | B1 | 9 | reddish purple +++ |
| A7 | B2 | 9 | crimson +++ |
| A7 | B3 | 9 | crimson +++ |
| A7 | B4 | 9 | yellow-orange ++ |
| A8 | B1 | 9 | purplish red +++ |
| A8 | B2 | 9 | chestnut +++ |
| A8 | B3 | 9 | chestnut +++ |
| A8 | B4 | 9 | orange-yellow ++ |
| A9 | B1 | 9 | reddish purple +++ |
| A9 | B2 | 9 | chestnut +++ |
| A9 | B3 | 9 | reddish purple +++ |
| A9 | B4 | 9 | orange ++ |

Intensity:
+++ = high
++ = moderate
+ = low
A1 3-[(dimethylamino)methyl]-4-hydroxy-5-methoxybenzaldehyde
A2 4-hydroxy-3-methoxy-5-(pyrrolidin-1-ylmethyl)benzaldehyde
A3 4-hydroxy-3-methoxy-5-(piperidin-1-ylmethyl)benzaldehyde
A4 4-hydroxy-3-methoxy-5-(morpholin-4-ylmethyl)benzaldehyde
A5 3-chloro-5-[(dimethylamino)methyl]-4-hydroxybenzaldehyde
A6 3-bromo-5-[(dimethylamino)methyl]-4-hydroxybenzaldehyde
A7 2,3,4-trihydroxy-5-(pyrrolidin-1-ylmethyl)benzaldehyde
A8 2,3,4-trihydroxy-5-(piperidin-1-ylmethyl)benzaldehyde
A9 2,3,4-trihydroxy-5-(morpholin-4-ylmethyl)benzaldehyde
B1 1,2-dihydro-1,3,4,6-tetramethyl-2-oxopyrimidinium hydrogensulfate
B2 1-allyl-1,2-dihydro-3,4,6-trimethyl-2-oxopyrimidinium bromide
B3 1,2-dihydro-1-(2-hydroxyethyl)-3,4,6-trimethyl-2-oxopyrimidinium-p-toluenesulfonate
B4 2-(cyanomethyl)benzimidazole While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. An agent for dyeing keratin-containing fibers, the agent comprising, in a cosmetic carrier:
as a component A at least one compound according to formula I,

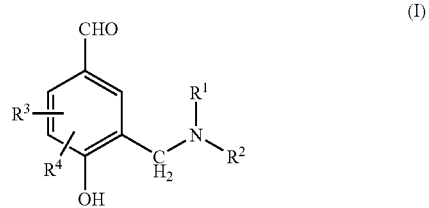

in which:
$R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and
$R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5 R^6$ group,
in which $R^5$ and $R^6$ mutually independently denote a ($C_1$ to $C_6$) alkyl group or a ($C_2$ to $C_6$) monohydroxyalkyl group and n denotes an integer from 0 to 6;
or $R^3$ and $R^4$ may form a five-membered or six-membered aromatic or heteroaromatic ring; and
at least one CH-acidic compound as a component B.

2. The agent as claimed in claim 1, wherein the residues $R^1$ and $R^2$ mutually independently denote a ($C_1$ to $C_6$) alkyl group, a ($C_1$ to $C_6$) monohydroxyalkyl group or an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted, and optionally contains at least one additional heteroatom selected from nitrogen, oxygen or sulfur.

3. The agent of claim 1, wherein $R^1$ and $R^2$ mutually independently denote a ($C_1$ to $C_6$) alkyl group or $R^1$ and $R^2$ form together with the nitrogen atom a group of the formula (I-1), (I-2) or (I-3)

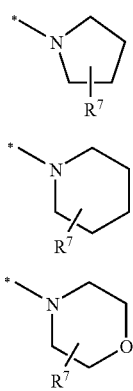

in which $R^7$ is a hydrogen atom, a halogen atom, a hydroxy group, a ($C_1$ to $C_6$) alkyl group, a ($C_1$ to $C_6$) monohydroxyalkyl group, a ($C_2$ to $C_6$) polyhydroxyalkyl group, a ($C_1$ to $C_6$) alkoxy group, or an amino group.

4. The agent of claim 1, wherein $R^4$ is a hydrogen atom or a hydroxy group, and $R^3$ denotes a fluorine atom, a chlorine atom, a bromine atom, an iodine atom, a hydroxy group or a ($C_1$ to $C_6$) alkoxy group or $R^3$ and $R^4$ together with the remainder of the molecule form a five-membered or six-membered aromatic or heteroaromatic ring.

5. The agent of claim 1, wherein the agent comprises at least one of the following compounds according to the formula (I):

3-[(dimethylamino)methyl]-4-hydroxy-5-methoxybenzaldehyde,
4-hydroxy-3-methoxy-5-(pyrrolidin-1-ylmethyl)benzaldehyde,
4-hydroxy-3-methoxy-5-(piperidin-1-ylmethyl)benzaldehyde,
4-hydroxy-3-methoxy-5-(morpholin-4-ylmethyl)benzaldehyde,
4-hydroxy-3-[(3-hydroxypyrrolidin-1-yl)methyl]-5-methoxybenzaldehyde,
4-hydroxy-3-[(4-hydroxypiperidin-1-yl)methyl]-5-methoxybenzaldehyde,
4-hydroxy-3-[(3-hydroxypiperidin-1-yl)methyl]-5-methoxybenzaldehyde,
3-bromo-5-[(dimethylamino)methyl]-4-hydroxybenzaldehyde,
3-bromo-4-hydroxy-5-(pyrrolidin-1-ylmethyl)benzaldehyde,
3-bromo-4-hydroxy-5-(piperidin-1-ylmethyl)benzaldehyde,
3-bromo-4-hydroxy-5-(morpholin-4-ylmethyl)benzaldehyde,
3-bromo-4-hydroxy-5-[(3-hydroxypyrrolidin-1-yl)methyl]-benzaldehyde,
3-bromo-4-hydroxy-5-[(4-hydroxypiperidin-1-yl)methyl]benzaldehyde,
3-bromo-4-hydroxy-5-[(3-hydroxypiperidin-1-yl)methyl]benzaldehyde,
3-chloro-5-[(dimethylamino)methyl]-4-hydroxybenzaldehyde,
3-chloro-4-hydroxy-5-(pyrrolidin-1-ylmethyl)benzaldehyde,
3-chloro-4-hydroxy-5-(piperidin-1-ylmethyl)benzaldehyde,
3-chloro-4-hydroxy-5-(morpholin-4-ylmethyl)benzaldehyde,
3-chloro-4-hydroxy-5-[(3-hydroxypyrrolidin-1-yl)methyl]-benzaldehyde,
3-chloro-4-hydroxy-5-[(4-hydroxypiperidin-1-yl)methyl]benzaldehyde,
3-chloro-4-hydroxy-5-[(3-hydroxypiperidin-1-yl)methyl]benzaldehyde,
3-[(dimethylamino)methyl]-4-hydroxy-1-naphthaldehyde,
4-hydroxy-3-(pyrrolidin-1-ylmethyl)-1-naphthaldehyde,
4-hydroxy-3-(piperidin-1-ylmethyl)-1-naphthaldehyde,
4-hydroxy-3-(morpholin-4-ylmethyl)-1-naphthaldehyde,
4-hydroxy-3-[(3-hydroxypyrrolidin-1-yl)methyl]-1-naphthaldehyde,
4-hydroxy-3-[(4-hydroxypiperidin-1-yl)methyl]-1-naphthaldehyde,
4-hydroxy-3-[(3-hydroxypiperidin-1-yl)methyl]-1-naphthaldehyde,
5-[(dimethylamino)methyl]-2,3,4-trihydroxybenzaldehyde,
2,3,4-trihydroxy-5-(pyrrolidin-1-ylmethyl)benzaldehyde,
2,3,4-trihydroxy-5-(piperidin-1-ylmethyl)benzaldehyde,
2,3,4-trihydroxy-5-(morpholin-4-ylmethyl)benzaldehyde,
3-[(dimethylamino)methyl]-2,4,5-trihydroxybenzaldehyde,
2,4,5-trihydroxy-3-(pyrrolidin-1-ylmethyl)benzaldehyde,
2,4,5-trihydroxy-3-(piperidin-1-ylmethyl)benzaldehyde, or
2,4,5-trihydroxy-3-(morpholin-4-ylmethyl)benzaldehyde.

6. The agent of claim 1, wherein the at least one CH-acidic compounds comprises a compounds of formula (II) or the enamine form thereof, a compound of formula (III), or a combination thereof:

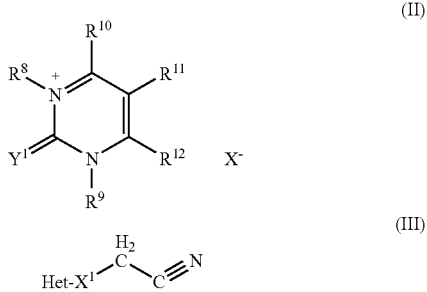

in which:
$R^8$ and $R^9$ mutually independently denote a linear or cyclic $C_1$-$C_6$ alkyl group, a $C_2$-$C_6$ alkenyl group, an optionally substituted aryl group, an optionally substituted heteroaryl group, an aryl-$C_1$-$C_6$-alkyl group, a $C_1$-$C_6$ hydroxyalkyl group, a $C_2$-$C_6$ polyhydroxyalkyl group, a $C_1$-$C_6$-alkoxy-$C_1$-$C_6$-alkyl group, an $R^{IV}R^VN$—$(CH_2)_m$— group, in which $R^{IV}$ and $R^V$ mutually independently denote a hydrogen atom, a $C_1$-$C_4$ alkyl group, a $C_1$-$C_4$ hydroxyalkyl group, or an aryl-$C_1$-$C_6$-alkyl group, wherein $R^{IV}$ and $R^V$, together with the nitrogen atom, optionally form a 5-, 6- or 7-membered ring and m denotes a number 2, 3, 4, 5 or 6;

R¹⁰ and R¹² mutually independently denote a hydrogen atom or a $C_1$-$C_6$ alkyl group, at least one of the residues R¹⁰ and R¹² comprising a $C_1$-$C_6$ alkyl group;

R¹¹ denotes a hydrogen atom, a $C_1$-$C_6$ alkyl group, a $C_1$-$C_6$ hydroxyalkyl group, a $C_2$-$C_6$ polyhydroxyalkyl group, a $C_1$-$C_6$ alkoxy group, a $C_1$-$C_6$ hydroxyalkoxy group, an $R^{VI}R^{VII}N$—$(CH_2)_q$— group, in which $R^{VI}$ and $R^{VII}$ mutually independently denote a hydrogen atom, a $C_1$-$C_6$ alkyl group, a $C_1$-$C_6$ hydroxyalkyl group or an aryl-$C_1$-$C_6$-alkyl group, and q denotes a number 1, 2, 3, 4, 5 or 6, or the residue R¹¹, together with one of the residues R¹⁰ or R¹², form a 5- or 6-membered aromatic ring, which optionally is substituted with a halogen atom, a ($C_1$-$C_6$) alkyl group, a $C_1$-$C_6$ hydroxyalkyl group, a $C_2$-$C_6$ polyhydroxyalkyl group, a ($C_1$-$C_6$) alkoxy group, a $C_1$-$C_6$ hydroxyalkoxy group, a nitro group, a hydroxy group, an $R^{VIII}R^{IX}N$—$(CH_2)_s$— group, in which $R^{VIII}$ and $R^{IX}$ mutually independently denote a hydrogen atom, a $C_1$-$C_6$ alkyl group, a $C_1$-$C_6$ hydroxyalkyl group or an aryl-$C_1$-$C_6$-alkyl group, and s denotes a number 0, 1, 2, 3, 4, 5 or 6;

Y¹ denotes an oxygen atom, a sulfur atom or an $NR^X$ group, in which $R^X$ denotes a hydrogen atom, an aryl group, a heteroaryl group, a $C_1$-$C_6$ alkyl group or a $C_1$-$C_6$ arylalkyl group;

X⁻ denotes a physiologically acceptable anion;

Het denotes an optionally substituted heteroaromatic and X¹ denotes a direct bond or a carbonyl group.

7. The agent of claim 1, wherein the component B CH-acidic compound comprises:

1H-benzimidazole-2-ylacetonitrile [2-(cyanomethyl)benzimidazole], and/or at least one compound selected from a group of salts with a physiologically acceptable counterion X⁻, which salts are formed from:

1,2-dihydro-1,3,4,6-tetramethyl-2-oxopyrimidinium,
1,2-dihydro-1,3-diethyl-4,6-dimethyl-2-oxopyrimidinium,
1,2-dihydro-1,3-dipropyl-4,6-dimethyl-2-oxopyrimidinium,
1,2-dihydro-1,3-di(2-hydroxyethyl)-4,6-dimethyl-2-oxopyrimidinium,
1,2-dihydro-1,3-diphenyl-4,6-dimethyl-2-oxopyrimidinium,
1,2-dihydro-1,3,4-trimethyl-2-oxopyrimidinium,
1,2-dihydro-1,3-diethyl-4-methyl-2-oxopyrimidinium,
1,2-dihydro-1,3-dipropyl-4-methyl-2-oxopyrimidinium,
1,2-dihydro-1,3-di(2-hydroxyethyl)-4-methyl-2-oxopyrimidinium,
1,2-dihydro-1,3-diphenyl-4-methyl-2-oxopyrimidinium,
1-allyl-1,2-dihydro-3,4,6-trimethyl-2-oxopyrimidinium,
1,2-dihydro-1-(2-hydroxyethyl)-3,4,6-trimethyl-2-oxopyrimidinium,
1,2-dihydro-1,3,4,6-tetramethyl-2-thioxopyrimidinium,
1,2-dihydro-1,3-diethyl-4,6-dimethyl-2-thioxopyrimidinium,
1,2-dihydro-1,3-dipropyl-4,6-dimethyl-2-thioxopyrimidinium,
1,2-dihydro-1,3-di(2-hydroxyethyl)-4,6-dimethyl-2-thioxopyrimidinium,
1,2-dihydro-1,3-diphenyl-4,6-dimethyl-2-thioxopyrimidinium,
1,2-dihydro-1,3,4-trimethyl-2-thioxopyrimidinium,
1,2-dihydro-1,3-diethyl-4-methyl-2-thioxopyrimidinium,
1,2-dihydro-1,3-dipropyl-4-methyl-2-thioxopyrimidinium,
1,2-dihydro-1,3-di(2-hydroxyethyl)-4-methyl-2-thioxopyrimidinium,
1,2-dihydro-1,3-diphenyl-4-methyl-2-thioxopyrimidinium,
1,2-dihydro-3,4-dimethyl-2-oxoquinazolinium and
1,2-dihydro-3,4-dimethyl-2-thioxoquinazolinium.

8. The agent of claim 1, further comprising as a component C at least one reactive carbonyl compound which is selected from the group consisting of 4-hydroxy-3-methoxybenzaldehyde, 3,5-dimethoxy-4-hydroxybenzaldehyde, 4-hydroxy-1-naphthaldehyde, 4-hydroxy-2-methoxybenzaldehyde, 3,4-dihydroxy-5-methoxybenzaldehyde, 3,4,5-trihydroxybenzaldehyde, 3,5-dibromo-4-hydroxybenzaldehyde, 4-hydroxy-3-nitrobenzaldehyde, 3-bromo-4-hydroxybenzaldehyde, 4-hydroxy-3-methylbenzaldehyde, 3,5-dimethyl-4-hydroxybenzaldehyde, 5-bromo-4-hydroxy-3-methoxybenzaldehyde, 4-diethylamino-2-hydroxybenzaldehyde, 4-dimethylamino-2-methoxybenzaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 4-dimethylaminobenzaldehyde, 4-diethylaminobenzaldehyde, 4-dimethylamino-2-hydroxybenzaldehyde, 4-pyrrolidinobenzaldehyde, 4-morpholinobenzaldehyde, 2-morpholinobenzaldehyde, 4-piperidinobenzaldehyde, 3,5-dichloro-4-hydroxybenzaldehyde, 4-hydroxy-3,5-diiodobenzaldehyde, 3-chloro-4-hydroxybenzaldehyde, 5-chloro-3,4-dihydroxybenzaldehyde, 5-bromo-3,4-dihydroxybenzaldehyde, 3-chloro-4-hydroxy-5-methoxybenzaldehyde, 4-hydroxy-3-iodo-5-methoxybenzaldehyde, 2-methoxy-1-naphthaldehyde, 4-methoxy-1-naphthaldehyde, 2-hydroxy-1-naphthaldehyde, 2,4-dihydroxy-1-napthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-dimethylamino-1-naphthaldehyde, 3-hydroxy-4-nitrobenzaldehyde, 2-hydroxy-3-methoxy-5-nitrobenzaldehyde, 5-nitrovanillin, 2,5-dinitrosalicylaldehyde, 5-bromo-3-nitrosalicylaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 3-allyl-4-hydroxybenzaldehyde, 3-allyl-4-hydroxy-5-methoxybenzaldehyde, 3-allyl-4-hydroxy-5-methylbenzaldehyde, 3-allyl-5-bromo-4-hydroxybenzaldehyde, 3,5-diallyl-4-hydroxybenzaldehyde, 3-allyl-4-hydroxy-5-formylbenzaldehyde (5-allyl-4-hydroxyisophthalaldehyde), and piperonal.

9. The agent of claim 8, wherein the component A, the component B and, optionally, the component C are present in the agent in a quantity of from about 0.03 to about 65 mmol, relative to 100 g of the total agent.

10. The agent of claim 1, further comprising a color enhancers selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylimidazole, arginine, histidine, pyrrolidine, proline, pyrrolidone, pyrrolidone-5-carboxylic acid, pyrazole, 1,2,4-triazole, piperazidine, and any desired mixtures thereof.

11. The agent of claim 1, further comprising an oxidizing agent in a quantity of from about 0.01 to about 6 wt. % relative to the total agent.

12. The agent of claim 1, further comprising as an oxidation dye precursor a developer component and, optionally, at least one coupler component.

13. The agent of claim 1, further comprising a direct dye.

14. The agent of claim 1, further comprising an anionic, zwitterionic or nonionic surfactants.

15. A method of dyeing keratin-containing fibers, comprising the steps of:
applying to the kaeratin-containing fibers an agent comprising, in a cosmetic carrier,
as a component A a compound according to formula (I)

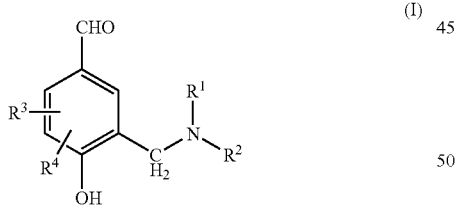

in which:
$R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and
$R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_1$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5 R^6$ group, in which $R^5$ and $R^6$ mutually independently denote a ($C_1$ to $C_6$) alkyl group or a ($C_2$ to $C_6$) monohydroxyalkyl group and n denotes an integer from 0 to 6; or $R^3$ and $R^4$ may form a five-membered or six-membered aromatic or heteroaromatic ring; and at least one CH— acidic compounds as a component B;
leaving the agent on the keratin-containing fibers for a period of time; and
rinsing the agent out of the keratin-containing fibers or washing the agent out of the keratin-containing fibers with a shampoo.

16. The method of claim 15, wherein, keratin-containing fibers were bleached with a bleaching preparation or dyed with an oxidation dyeing agent before application of the agent.

17. A method for shading oxidation dyed keratin-containing fibers, comprising the step of:
applying to the keratin-containing fibers an agent comprising:
as a component A at least one compound according to formula I,

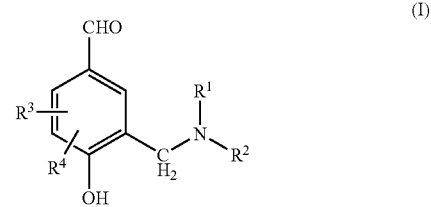

in which:
$R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and
$R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_1$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5 R^6$ group, in which $R^5$ and $R^6$ mutually independently denote a ($C_1$ to $C_6$) alkyl group or a ($C_2$ to $C_6$) monohydroxyalkyl group and n denotes an integer from 0 to 6; or $R^3$ and $R^4$ may form a five-membered or six-membered aromatic or heteroaromatic ring; and at least on CH— acidic compound as component B.

18. A method for freshening up keratin-containing fibers dyed with an oxidative dyeing agent, the method comprising the steps of:

applying to the keratin-containing fibers an agent comprising:

as a component A at least one compound according to formula I,

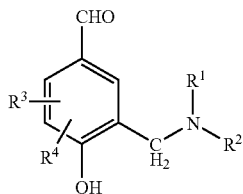

(I)

in which
- $R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ to $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and
- $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_2$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5R^6$ group, in which $R^5$ and $R^6$ mutually independently denote a ($C_1$ to $C_6$) alkyl group or a ($C_2$ to $C_6$) monohydroxyalkyl group and n denotes an integer from 0 to 6; or $R^3$ and $R^4$ may form a five-membered or six-membered aromatic or heteroaromatic ring; and at least one CH-acidic compound as a component B.

19. The agent of claim 9, wherein the component A, the component B and, optionally, the component C, are present in the agent in a quantity of from about 1 to about 40 mmol, relative to 100 g of the total agent.

20. The agent of claim 11, wherein the oxidizing agent comprises $H_2O_2$.

21. The agent of claim 13, wherein the agent comprises a direct dye in a quantity of from about 0.01 to about 20 wt. % relative to the total agent.

22. A method for making an agent for dyeing keratin-containing fibers comprising the steps of:

providing a compound according to formula (I)

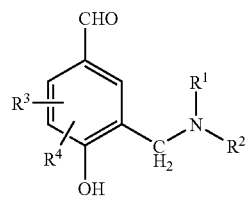

(I)

in which:
- $R^1$ and $R^2$ mutually independently denote a ($C_1$ to $C_6$) alkyl group, a ($C_2$ to $C_6$) alkenyl group, a ($C_1$ to $C_6$) monohydroxyalkyl group, a ($C_2$ to $C_6$) polyhydroxyalkyl group, a ($C_1$ to $C_6$)-alkoxy-($C_2$ $C_6$)-alkyl group, an aryl-($C_1$ to $C_6$)-alkyl group or the two residues form together with the nitrogen atom a five-membered, six-membered, seven-membered or eight-membered heterocyclic ring, which is saturated or unsaturated, is optionally substituted and optionally contains at least one additional heteroatom selected from nitrogen, oxygen or sulfur; and
- $R^3$ and $R^4$ mutually independently denote a hydrogen atom, a halogen atom, a ($C_1$ to $C_6$) alkyl group, a ($C_2$ to $C_6$) alkenyl group, a hydroxy group, a ($C_1$ to $C_6$) alkoxy group, a ($C_1$ to $C_6$) monohydroxyalkyl group, a ($C_1$ to $C_6$) polyhydroxyalkyl group, a hydroxy-($C_1$ to $C_6$)-alkyloxy group, a piperidin-1-ylmethyl group, a pyrrolidin-1-ylmethyl group, a morpholin-4-ylmethyl group or a —$(CH_2)_n NR^5R^6$ group, in which $R^5$ and $R^6$ mutually independently denote a ($C_1$ to $C_6$) alkyl group or a ($C_2$ to $C_6$) monohydroxyalkyl group and n denotes an integer from 0 to 6, or $R^3$ and $R^4$ may form a five-membered or six-membered aromatic or heteroaromatic ring; and combining the compound according to formula (I) with at least one CH— acidic compound.

* * * * *